US009884891B2

(12) United States Patent
Beltramo et al.

(10) Patent No.: US 9,884,891 B2
(45) Date of Patent: Feb. 6, 2018

(54) KISS1R RECEPTOR AGONIST COMPOUNDS AND USE THEREOF FOR INDUCING OVULATION IN MAMMALS

(71) Applicants: INSTITUT NATIONAL DE LA RECHERCHE AGRONOMIQUE, Paris (FR); CENTRE NATIONAL DE LA RECHERCHE SCIENTIFIQUE, Paris (FR)

(72) Inventors: Massimiliano Beltramo, Monthodon (FR); Vincent Aucagne, Fleury les Aubrais (FR); Alain Caraty, Veigne (FR); Agnes Delmas, Orleans (FR); Mathieu Galibert, Orleans (FR)

(73) Assignees: INSTITUT NATIONAL DE LA RECHERCHE AGRONOMIQUE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/765,251

(22) PCT Filed: Jan. 31, 2014

(86) PCT No.: PCT/EP2014/051886
§ 371 (c)(1),
(2) Date: Jul. 31, 2015

(87) PCT Pub. No.: WO2014/118318
PCT Pub. Date: Aug. 7, 2014

(65) Prior Publication Data
US 2015/0361138 A1 Dec. 17, 2015

(30) Foreign Application Priority Data

Jan. 31, 2013 (FR) ...................... 13 50858

(51) Int. Cl.
*A61K 38/14* (2006.01)
*A61K 38/00* (2006.01)
*A61K 38/04* (2006.01)
*A61K 38/06* (2006.01)
*A61K 38/07* (2006.01)
*A61K 38/08* (2006.01)
*C07K 5/00* (2006.01)
*C07K 7/00* (2006.01)
*C07K 9/00* (2006.01)
*C07K 16/00* (2006.01)
*C07K 17/00* (2006.01)
*C07K 7/06* (2006.01)
*C07K 5/02* (2006.01)
*C07K 7/02* (2006.01)
*C07K 14/575* (2006.01)

(52) U.S. Cl.
CPC .............. *C07K 7/06* (2013.01); *A61K 38/07* (2013.01); *A61K 38/08* (2013.01); *C07K 5/02* (2013.01); *C07K 7/00* (2013.01); *C07K 7/02* (2013.01); *C07K 14/575* (2013.01); *A61K 38/00* (2013.01)

(58) Field of Classification Search
None
See application file for complete search history.

(56) References Cited

U.S. PATENT DOCUMENTS

2006/0241051 A1* 10/2006 Kitada .................. C07K 14/47
514/1.3

FOREIGN PATENT DOCUMENTS

WO    2005117939    12/2005
WO    2013017631    2/2013

OTHER PUBLICATIONS

Feldman et al., Org. Letters 6:3897-3899 (2004).*
Bock et al., Org. Biomol. Chem. 5:971-975 (2007).*
Li et al., Molecules 18:9797-9817 (2013).*
Angelini et al., "Bicyclization and Tethering to Albumin Yields Long-Acting Peptide Antagonists", 2012, Journal of Medicinal Chemistry, vol. 55: pp. 10187-10197.
A. Caraty et al., "Kisspeptin Synchronizes Preovulatory Surges in Cyclical Ewes and Causes Ovulation in Seasonally Acyclic Ewes", 2007, Endocrinology 148(11): 5258-5267.
A. Caraty and I. Franceschini, "Basic Aspects of the Control of GnRH and LH Secretions by Kisspeptin: Potential Applications for Better Control of Fertility in Females", 2008, Reprod. Dom. Anim. 43 (Suppl. 2): pp. 172-178.
Dennis et al., "Albumin Binding as a General Strategy for Improving the Pharmacokinetics of Proteins", 2002, J. Biol. Chem., vol. 277, No. 38, Issue of Sep. 20, pp. 35035-35043.
Dumelin et al., "A Portable Albumin Binder from a DNA-Encoded Chemical Library", Angew. Chem. Int. Ed., 2008, 47, pp. 3196-3201.
Goddard-Borger et al., "An Efficient, Inexpensive, and Shelf-Stable Diazotransfer Reagent: Imidazole-1-sulfonyl Azide Hydrochloride", 2007, American Chemical Society, Organic Letters, vol. 9, No. 19, pp. 3797-3800.
Knudsen et al., "Potent Derivatives of Glucagon-like Peptide-1 with Pharmacokinetic Properties Suitable for Once Daily Administration", J. Med. Chem. 2000, 43, pp. 1664-1669.
Kotani et al., "The Metastasis Suppressor Gene KiSS-1 Encodes Kisspeptins, the Natural Ligands of the Orphan G Protein-coupled Receptor GPR54", J. Biol. Chem., vol. 276, No. 37, Issue of Sep. 17, pp. 34631-34636, (2001).

(Continued)

*Primary Examiner* — Hasan S Ahmed
*Assistant Examiner* — Thea D'Ambrosio
(74) *Attorney, Agent, or Firm* — Young & Thompson

(57) ABSTRACT

A KISS1R agonist peptide compound capable of inducing ovulation in a female mammal is provided. The compound is a pseudopeptide having the C-terminal sequence: -Xaa1Ψ[Tz]Xaa2-Xaa3-Xaa4-NH$_2$ (SEQ ID NO: 3), where Ψ[Tz] represents a 1,4-disubstituted 1,2,3-triazole group replacing the peptide bond between the Xaa1 residue and the Xaa2 residue, Xaa1 is Gly or Ala, Xaa2 is Leu or an aliphatic α-aminoacyl analog residue, Xaa3 is Arg, Arg(Me) or a positively charged α-aminoacyl analog residue, and Xaa4 is Tyr, Phe, Trp or an α-aminoacyl analog residue such as aryl alanine; or an analog of the pseudopeptide in which the amide peptide bond between Xaa2 and Xaa3 and/or between Xaa3 and Xaa4 is replaced with an isosteric bond, or a salt thereof.

16 Claims, 7 Drawing Sheets

(56) References Cited

OTHER PUBLICATIONS

Mancini et al., Themed Issue: GPCR, Research Paper, "Constitutive activity of cannabinoid-2 (CB2) receptors play an essential role in the protean agonism of (+)AM1241 and L768242", British Journal of Pharmacology (2009), 158, pp. 382-391.
Pokorski et al., "Introduction of a Triazole Amino Acid into a Peptoid Oligomer Induces Turn Formation in Aqueous Solution", 2007, Org. Lett., vol. 9, No. 12, pp. 2381-2383.
Reginato et al., "A New Stereoselective Synthesis of Chiral y-Functionalized (E)-Allylic Amines", 1996, Tetrahedron, vol. 52, No. 33, pp. 10985-10996.
Sébert et al., "Insights into the mechanism by which kisspeptin stimulates a preovulatory LH surge and ovulation in seasonally acyclic ewes: Potential role of estradiol", 2010, Domest. Anim. Endocrinol. 38, pp. 289-298.
Seminara et al., "Continuous Human Metastin 45-54 Infusion Desensitizes G Protein-Coupled Receptor 54-Induced Gonadotropin-Releasing Hormone Release Monitored Indirectly in the Juvenile Male Rhesus Monkey (*Macaca mulatta*): A Finding with Therapeutic Implications", 2006, Endocrinology 147(5): 2122-2126.
Trússel et al., "New Strategy for the Extension of the Serum Half-Life of Antibody Fragments", 2009, Bioconjugate Chem., 20: pp. 2286-2292.
Zarandi et al., "Lipopeptide antagonists of growth hormone-releasing hormone with improved antitumor activities", Mar. 21, 2006, Proc. Natl. Acad. Sci. USA, vol. 103, No. 12, pp. 4610-4615.
Zhang et al., "Hypothalamic Programming of Systemic Aging Involving IKKβ/NF-KB and GnRH", 2013, Nature 497 (7448): 211-216.

\* cited by examiner

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial sequence
<220> FEATURE:
<223> OTHER INFORMATION: Mouse-derived kisspeptin-10
<220> FEATURE:
<221> NAME/KEY: MOD_RES
<222> LOCATION: (10)..(10)
<223> OTHER INFORMATION: AMIDATION

<400> SEQUENCE: 1

Tyr Asn Trp Asn Ser Phe Gly Leu Arg Tyr
1               5                   10

<210> SEQ ID NO 2
<211> LENGTH: 10
```

```
<212> TYPE: PRT
<213> ORGANISM: Artificial sequence
<220> FEATURE:
<223> OTHER INFORMATION: Human-derived kisspeptin-10
<220> FEATURE:
<221> NAME/KEY: MOD_RES
<222> LOCATION: (10)..(10)
<223> OTHER INFORMATION: AMIDATION

<400> SEQUENCE: 2

Tyr Asn Trp Asn Ser Phe Gly Leu Arg Phe
1               5                   10

<210> SEQ ID NO 3
<211> LENGTH: 4
<212> TYPE: PRT
<213> ORGANISM: Artificial sequence
<220> FEATURE:
<223> OTHER INFORMATION: C-terminal sequence of synthetic agonist of
      KISS1R
<220> FEATURE:
<221> NAME/KEY: MISC_FEATURE
<222> LOCATION: (1)..(2)
<223> OTHER INFORMATION: Substitution of peptide bond by
      1,4-disubstituted 1,2,3-triazole
<220> FEATURE:
<221> NAME/KEY: NON_TER
<222> LOCATION: (1)..(1)
<220> FEATURE:
<221> NAME/KEY: MISC_FEATURE
<222> LOCATION: (1)..(1)
<223> OTHER INFORMATION: Xaa is Gly or Ala
<220> FEATURE:
<221> NAME/KEY: MISC_FEATURE
<222> LOCATION: (2)..(2)
<223> OTHER INFORMATION: Xaa is Leu or an aliphatic alpha-amino acyl
      analog residue
<220> FEATURE:
<221> NAME/KEY: MISC_FEATURE
<222> LOCATION: (3)..(3)
<223> OTHER INFORMATION: Xaa is Arg, Arg(Me) or a positively charged
      alpha-amino acyl analog residue
<220> FEATURE:
<221> NAME/KEY: MISC_FEATURE
<222> LOCATION: (4)..(4)
<223> OTHER INFORMATION: Xaa is Tyr, Phe, Trp or an alpha-amino acyl
      analog residue of the aryl alanine type
<220> FEATURE:
<221> NAME/KEY: MOD_RES
<222> LOCATION: (4)..(4)
<223> OTHER INFORMATION: AMIDATION

<400> SEQUENCE: 3

Xaa Xaa Xaa Xaa
1

<210> SEQ ID NO 4
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MISC_FEATURE
<222> LOCATION: (7)..(7)
<223> OTHER INFORMATION: Xaa is Gly or Ala
<220> FEATURE:
<221> NAME/KEY: MISC_FEATURE
<222> LOCATION: (8)..(8)
<223> OTHER INFORMATION: Xaa is Leu or an aliphatic alpha-amino acyl
```

```
      analog residue
<220> FEATURE:
<221> NAME/KEY: MISC_FEATURE
<222> LOCATION: (9)..(9)
<223> OTHER INFORMATION: Xaa is Arg, Arg(Me) or a positively charged
      alpha-amino acyl analog residue
<220> FEATURE:
<221> NAME/KEY: MISC_FEATURE
<222> LOCATION: (10)..(10)
<223> OTHER INFORMATION: Xaa is Tyr, Phe, Trp or an alpha-amino acyl
      analog residue of the aryl alanine type
<220> FEATURE:
<221> NAME/KEY: MOD_RES
<222> LOCATION: (10)..(10)
<223> OTHER INFORMATION: AMIDATION

<400> SEQUENCE: 4

Tyr Asn Trp Asn Ser Phe Xaa Xaa Xaa Xaa
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 5

Tyr Asn Trp Asn Ser Phe Gly Leu Arg Tyr
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 6

Tyr Asn Trp Asn Ser Phe Gly Leu Arg Tyr
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (10)..(10)
<223> OTHER INFORMATION: AMIDATION

<400> SEQUENCE: 7

Tyr Asn Trp Asn Ser Phe Gly Leu Arg Tyr
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: ACETYLATION
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 8

Tyr Asn Lys Asn Ser Phe Gly Leu Arg Tyr
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(7)
<223> OTHER INFORMATION: Substitution of peptide bond by
      1,4-disubstituted 1,2,3-triazole
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 9

Tyr Asn Trp Asn Ser Phe Gly Leu Arg Tyr
```

<210> SEQ ID NO 10
<211> LENGTH: 10
<212> TYPE: PRT
<213> ORGANISM: Artificial sequence
<220> FEATURE:
<223> OTHER INFORMATION: Synthetic mouse-derived kisspeptin-10
    derivative
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 10

Tyr Asn Trp Asn Ser Phe Gly Leu Arg Tyr
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Side chain modification by gamma-(N-
    hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
    1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 11

Tyr Lys Trp Asn Ser Phe Gly Leu Arg Tyr
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (1)..(1)
<223> OTHER INFORMATION: N-terminal modification by gamma-(N-
    hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
    1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 12

```
Tyr Asn Trp Asn Ser Phe Gly Leu Arg Tyr
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (1)..(1)
<223> OTHER INFORMATION: N-terminal modification by gamma-(N-
      hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 13

Tyr Asn Trp Asn Ser Phe Gly Leu Arg Trp
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Side chain modification by gamma-(N-
      hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 14

Tyr Asn Lys Asn Ser Phe Gly Leu Arg Tyr
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (1)..(1)
<223> OTHER INFORMATION: N-terminal modification by gamma-(N-
      hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
```

```
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (10)..(10)
<223> OTHER INFORMATION: AMIDATION

<400> SEQUENCE: 15

Tyr Asn Trp Asn Ser Phe Gly Leu Arg Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MISC_FEATURE
<222> LOCATION: (1)..(1)
<223> OTHER INFORMATION: N-terminal modification by gamma-(N-
      hexadecanoyl-L-glutamyle)
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 16

Tyr Asn Trp Asn Ser Phe Gly Leu Arg Phe
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Side chain modification by TTDS-(gamma-(N-
      hexadecanoyl-Glu-OH))
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 17

Tyr Lys Trp Asn Ser Phe Gly Leu Arg Tyr
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Side chain modification by
      2-(succinamido)-6-(4-(4-iodophenyl)butanamido)hexanoate
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 18

Tyr Lys Trp Asn Ser Phe Gly Leu Arg Tyr
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic agonist of KISS1R
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Side chain modification by polethylene glycol
      (PEG 5000)
<220> FEATURE:
<221> NAME/KEY: MISC_FEATURE
<222> LOCATION: (7)..(8)
<223> OTHER INFORMATION: Substitution of peptide bond by
      1,4-disubstituted 1,2,3-triazole
<220> FEATURE:
<221> NAME/KEY: MOD_RES
<222> LOCATION: (10)..(10)
<223> OTHER INFORMATION: AMIDATION

<400> SEQUENCE: 19

Tyr Lys Trp Asn Ser Phe Gly Leu Arg Tyr
1               5                   10
```

KISS1R RECEPTOR AGONIST COMPOUNDS AND USE THEREOF FOR INDUCING OVULATION IN MAMMALS

FIELD OF THE INVENTION

The present invention falls within the field of the induction and synchronization of ovulation in mammals. More particularly, it relates to a KISS1R receptor agonist peptide compound capable of inducing/synchronizing such an ovulation, and also to the use of such a compound as a medicament, in particular for inducing this ovulation, and to a veterinary and/or pharmaceutical composition containing same.

The compound according to the invention has in particular applications in the breeding field, in particular with a view to programming reproduction throughout the year, for example in members of the ovine race, members of the goat family, or cattle. Although the latter species is not of the type which reproduces seasonally, dairy cows nevertheless exhibit a drop in fertility and a KISS1R receptor agonist could be used to re-establish better fertility. Moreover, the compound according to the invention also has applications in the therapeutic field, in particular for reducing infertility problems, and in particular in human clinical practice for the treatment of reproductive pathological conditions, in particular in the context of the implementation of medically assisted procreation techniques. Other applications of this compound are the treatment of other pathological conditions, such as hypothalamic amenorrhea and delayed puberty, and any other pathological conditions which require an increase in the secretion of GnRH (for Gonadotropin Releasing Hormone) and of gonadotropins.

BACKGROUND OF THE INVENTION

In the breeding field, the control of reproduction is a considerable challenge, with a view to optimizing the availability of products, such as meat, milk or its derivatives, throughout the year. For example, the breeding of members of the ovine race and of the goat family is subjected to strong seasonal variations in productivity, owing to the seasonal nature of the reproduction and the course of lactation. The methods used at the current time for inducing ovulation at any time out of season and/or for synchronizing ovulation within herds and flocks rely on the use of steroid hormones, such as progesterone or estradiol, of prostaglandin F2a and of PMSG (Pregnant Mare Serum Gonadotropin). These methods do not, however, allow complete control of ovulation. In addition, the estrogen-type hormones used are pollutants which are not readily degraded, which accumulate in soil and water, and which present a threat to human health. The treatment of animals with such hormones also has considerable constraints for breeders, who are obliged to adhere to very strict specifications. By way of example, the methods used at the current time for inducing ovulation in ewes provide for the implantation, for 12 to 24 days, of a vaginal sponge containing progesterone, combined with a co-treatment with an intramuscular injection of PMSG serum gonadotropin at the time of withdrawal of the sponge. Such a treatment proves to be restricting to carry out.

In human clinical practice, the treatments available at the current time for medically assisted procreation have, for their part, certain undesirable side effects, such as ovarian hyperstimulation. These treatments also use hormones to induce ovulation, and therefore act either on the pituitary gland or on the gonads. The same is true for treatments intended to treat hypothalamic amenorrhea or delayed puberty.

There thus remains a need for alternative treatments, using a nonsteroidal molecule capable of triggering/synchronizing ovulation both in ruminants, so as to be able to program their reproduction and their milk production throughout the year, to improve artificial insemination yields, to optimize the profitability of herds and flocks, and to reduce infertility problems in herds and flocks, and in humans, for inducing gonadotropin release more naturally than the current hormonal treatments, thus reducing the risks of ovarian hyperstimulation syndrome.

The present invention aims to remedy the drawbacks of the treatments proposed by the prior art for inducing/synchronizing ovulation in female mammals, in particular those set out above, by providing a nonsteroidal compound which makes it possible to carry out such an ovulation induction/synchronization efficiently, and which exhibits low persistence in the environment, and reduced use constraints.

SUMMARY OF THE INVENTION

To this effect, the present inventors have been interested in the neurotransmission system formed by a receptor, KISS1R, also called KISS1 receptor, or GPR54 (GenBank accession No., for the human receptor: NM_032551.4, GI:189163516), and its endogenous ligands, called kisspeptides (or kisspeptins), resulting from the cleavage of a precursor peptide, KISS1 (GenBank accession No., for the human peptide: NM_002256.3, GI:116829963; NP_002247.3, GI:116829964; for the murine peptide: AB666166.1, GI:384367966; BAM11250.1, GI:384367967; for the ovine peptide: AFW03832.1, GI:411100741), which are neurotransmitters which have the capacity to stimulate KISS1R (Kotani et al., 2011).

In the present description, the abbreviation KISS1R will be used to denote both the human receptor and the receptor of the other species (indicated by the abbreviation Kiss1 r in the official nomenclature). A complete list of the synonyms used to denote KISS1R is in particular available on the IUPHAR website.

More particularly, the kisspeptide (kisspeptin) essentially responsible for the KISS1R stimulation biological activity is the decapeptide called kisspeptin-10, or KP10. The sequences of mouse-derived kisspeptin-10 (mKP10, of sequence SEQ ID NO:1, in which the C-terminal end is modified by amidation) and of human-derived kisspeptin-10 (hKP10, of sequence SEQ ID NO:2, in which the C-terminal end is modified by amidation) are in particular known. Ewe-derived kisspeptin-10 is in particular identical to mKP10.

The activation of KISS1R by its ligands, and more particularly by KP10, induces a very powerful stimulatory effect on the release of the hormones LH and FSH in mammals, this effect resulting from an increase in the secretion of GnRH (Gonadotropin Releasing Hormone) (Caraty and Franceschini, 2008). It has been shown in particular that KP10, administered intravenously to ewes at the end of the follicular phase, is capable of inducing an LH peak which is followed, 21 hours later, by ovulations synchronized to within one hour (Caraty et al., 2007). It has also been demonstrated that, during the period of sexual rest (seasonal anestrus), a prolonged infusion of KP10 is capable of reactivating the gonadotropic axis and inducing ovulation (Sébert et al., 2010). These results thus demonstrated the feasibility of controlling the ovulation of livestock animals through the stimulation of the KISS1R/KP10 system. Human KISS1R and ewe KISS1R also exhibit a very high degree of homology, with more than 60% identity, and the kisspeptides (kisspeptins) show a similar in vivo activity in primates and ewes (Seminara et al., 2006, Caraty et al., 2007), which makes it possible to envision an application in human therapy.

Compared with steroid hormones, KP10 has in particular the advantages of being very rapidly eliminated from the organism and easily destroyed in the natural environment, so as to leave only amino acids as residues. Moreover, it has a mechanism of action, resulting in a triggering of the secretion of the hormone LH, a hormone required for the induction of ovulation, which is completely different than that of the current treatments, and enabling a finer and more localized action while avoiding the undesirable side effects.

However, since KP10 is rapidly degraded and excreted by the organism, it has a limited duration of action. The present inventors have thus aimed to develop KP10-derived compounds which have a prolonged and controlled duration of action in the organism, while at the same time retaining properties of degradability in the environment that are similar to those of KP10. The invention also aims for these compounds to be capable of efficiently inducing ovulation in a female mammal, including out of season, with a low number of administrations, in particular with a single injection. An additional objective of the invention is for these compounds to have a low preparation cost.

It has now been discovered by the present inventors that such advantageous results are achieved by particular peptide compounds in which, in particular, a peptide bond between a glycine residue and the adjacent residue, located in a region close to the C-terminal end of the compound, is replaced with a disubstituted 1,2,3-triazole nucleus. In the present description, the positions of the amino acids in the peptides are defined in a manner which is conventional in itself, the numbering beginning at the N-terminal end of the peptide, appearing on the left in all the sequences, while the C-terminal end, for its part, appears on the right.

DETAILED DESCRIPTION OF THE INVENTION

Thus, the present invention provides a KISS1R agonist peptide compound chosen from:
a pseudopeptide, capable of binding KISS1R, having the C-terminal sequence:

-Xaa1Ψ[Tz]Xaa2-Xaa3-Xaa4-NH$_2$ (SEQ ID NO:3)

where
Ψ[Tz] represents a 1,4-disubstituted 1,2,3-triazole group of formula (I):

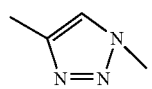

(I)

replacing the peptide bond between the Xaa1 residue and the Xaa2 residue,
the C-terminal end, at the level of the Xaa4 residue, is modified by amidation,
Xaa1 represents Gly or Ala,
Xaa2 represents Leu or an aliphatic α-aminoacyl analog residue, such as Ile, Val, Ala(cPr), Nle or Nval,
Xaa3 represents Arg, the —NH$_2$ function of which is, where appropriate, substituted with a methyl group, or a positively charged α-aminoacyl analog residue, such as Arg(asymMe$_2$), Lys, where appropriate substituted, or Orn, where appropriate substituted,
Xaa4 represents Tyr, Phe, Trp or an α-aminoacyl analog residue of aryl alanine type, such as 1-, 2- or 3-naphthylalanine, 2- or 3-thienylalanine, 2- or 3-furylalanine, 2-, 3- or 4-fluorophenylalanine, 2-, 3- or 4-chlorophenylalanine, 2-, 3- or 4-bromophenylalanine, 2-, 3- or 4-cyanophenylalanine, 2-, 3- or 4-iodophenylalanine, 2-, 3- or 4-methylphenylalanine or 2-, 3- or 4-trifluoromethylphenylalanine,
an analog of the pseudopeptide of sequence SEQ ID NO:3 in which the amide peptide bond between Xaa2 and Xaa3 and/or between Xaa3 and Xaa4 is replaced with an isosteric bond,
or a salt thereof.

The disubstituted 1,2,3-triazole nucleus advantageously constitutes an inexpensive and readily accessible isostere, so that the process for synthesizing such a compound is advantageously inexpensive to carry out. This synthesis can also be easily carried out by the conventional peptide synthesis techniques, for example on a solid phase using Fmoc/tBu strategy.

The peptide compound in accordance with the invention advantageously has, compared with KP10, a prolonged lifetime in the organism, more particularly in blood serum, while at the same time retaining a KISS1R-stimulating efficiency which is as high, or even better, and also a minimal environmental persistence. It makes it possible in particular to significantly increase the blood level of the hormone LH in mammals, including in the anestrus period, with a limited number of administrations, what is more via a route of administration which is in particular compatible with use in livestock, in particular by means of a single injection, for example intramuscular or subcutaneous injection.

In the present description, the expression "C-terminal region" will denote the region of the peptide compound of sequence SEQ ID NO:3, and the expression "N-terminal region" will denote the remaining region of the compound.

In particular embodiments of the invention, Xaa1 represents Gly, Xaa2 represents Leu and Xaa3 represents Arg, the —NH$_2$ function of which is, where appropriate, substituted with a methyl group.

The peptide compound according to the invention may have a size of from 5 to 54 amino acids, preferably from 5 to 16 amino acids, more preferably from 7 to 12 amino acids, and preferentially 9, 10 or 11 amino acids.

In particular embodiments of the invention, particularly advantageous in terms of length of half-life in blood serum, the peptide compound corresponds to one or more of the characteristics hereinafter:
at least the N-terminal amine function is modified by substitution with a group chosen from linear, in particular C$_1$-C$_6$, preferably C$_2$, alcanoyls, a benzoyl group and a tetramethylguanidinium group,
at least the N-terminal amine function is replaced with an azide function, or with a 1,4-disubstituted 1,2,3-triazole group of formula (I);
at least one amino acid, more particularly of the N-terminal region, is bonded to one or more polyalkylene glycol, preferably polyethylene glycol, chains, and/or to one or more lipid chains, such as a palmitoyl group, and/or groups which bind to serum albumin. Such modifications advantageously make it possible to increase the half-life of the peptide compound in the organism. In particular embodiments, at least one amino acid is bonded to a linear or branched polyethylene glycol chain having a molecular weight of between 5 and 40 kDa;

at least the N-terminal amine function is substituted with an alkyl group, in particular chosen from linear, preferably $C_1$-$C_6$, alkyls, in particular with a methyl group or with a benzyl group.

The peptide compound according to the invention may be cyclized, by any cross bond, which is conventional in itself, between the side chains of two amino acids of its N-terminal region and/or its N-terminal amine function, in particular by formation of an amide, of a triazole, of an alkene, of a disulfide bridge, of a bis-thioether, etc.

In particular embodiments of the invention, the peptide compound is chosen from:

a pseudopeptide of sequence:

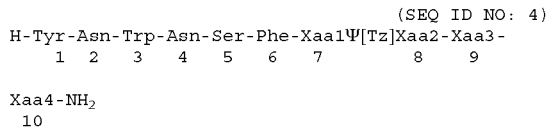

where Ψ[Tz], Xaa1, Xaa2, Xaa3 and Xaa4 are as previously defined, and the C-terminal end, at the level of the Xaa4 residue, is modified by amidation, an analog of said pseudopeptide of sequence SEQ ID NO:4 capable of binding KISS1R, or a salt thereof.

The expression "analog of the pseudopeptide of sequence SEQ ID NO:4 capable of binding KISS1R" is intended to mean any pseudopeptide having the C-terminal sequence SEQ ID NO:3, where the sequence of which differs from the sequence SEQ ID NO:4 by one or more modifications at the level of the N-terminal region, in particular by an addition, substitution, with a natural or unnatural amino acid, including D enantiomers, and/or deletion, of one or more amino acids, and/or by a modification of the N-terminal end and/or of any functional group borne by the side chain of an amino acid, and/or by the replacement of a peptide bond with an isosteric bond, while at the same time retaining the ability to bind KISS1R.

The ability of the peptide compounds to bind KISS1R can be tested in various ways. It can in particular be tested using an in vivo test, by measuring the LH concentration in blood samples from ewes previously injected with the test molecule, for example according to the protocol described hereinafter in the present description. An increase in this concentration, compared with a nontreated control, attests to an ability of the analog to bond KISS1R.

Moreover, this ability can be tested using an in vitro test, by measuring the amount of intracellular calcium in a cell line expressing KISS1R after incubation with the test molecule. This is because the stimulation of KISS1R results in the activation of two distinct intracellular pathways, which induce an increase in the intracellular concentration of calcium ions: by release from the intracellular stores, following the production of IP3, and by entry, following opening of the ion channels (for example TRPC) of the plasma membrane of the cell, of calcium ions present in the extracellular medium. An example of such a test, termed calcium mobilization test, is described in detail hereinafter in the present description. An increase in the amount of intracellular calcium, compared with a nontreated control, then attests to the ability of the analog to bind KISS1R.

Particular analogs of the pseudopeptide of sequence SEQ ID NO:4, having in particular a half-life in blood serum greater than that of KP10, correspond to one or more of the characteristics hereinafter:

at least one amino acid among Tyr1, Asn2 and Trp3, is replaced with a lysine, the amine function of which is preferably substituted with one or more groups chosen from an alkanoyl group, in particular an acetyl group, a polyalkylene glycol, preferably polyethylene glycol, chain, and a lipid chain, such as a palmitoyl group or another group enabling an interaction with serum albumin;

at least the amino acid Tyr1 is replaced with its D enantiomer.

Particular peptide compounds according to the invention are analogs of the pseudopeptide of sequence SEQ ID NO:4, which differ from the latter but conserve a serine (Ser) residue two positions upstream of Xaa1, that is to say in most cases, at position 5.

Other peptide compounds according to the invention have a threonine (Thr) residue at this position.

Particular peptide compounds in accordance with the present invention correspond to the sequences:

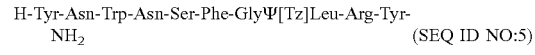

in which the C-terminal end is modified by amidation and the peptide bond between the glycine at position 7 and the leucine at position 8 is substituted with a 1,4-disubstituted 1,2,3-triazole group,

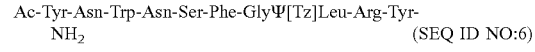

in which, in addition to the amidation at the C-terminal end and the substitution of the peptide bond between the glycine and the leucine with a 1,4-disubstituted 1,2,3-triazole group, the N-terminal end is modified by acetylation,

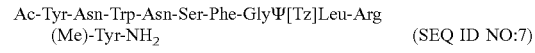

in which, in addition to the amidation at the C-terminal end and the substitution of the peptide bond between the glycine and the leucine with a 1,4-disubstituted 1,2,3-triazole group, the N-terminal end is modified by acetylation and the arginine residue at position 9 is modified by methylation,

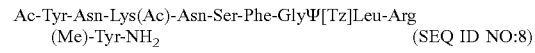

in which, in addition to the amidation at the C-terminal end and the substitution of the peptide bond between the glycine and the leucine with a 1,4-disubstituted 1,2,3-triazole group, the N-terminal end is modified by acetylation, the arginine residue at position 9 is modified by methylation and the lysine residue at position 3 is modified by acetylation,

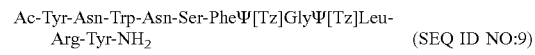

in which, in addition to the amidation at the C-terminal end and the substitution of the peptide bond between the glycine and the leucine with a 1,4-disubstituted 1,2,3-triazole group, the N-terminal end is modified by acetylation and the peptide bond between the phenylalanine at position 6 and the glycine at position 7 is also substituted with a 1,4-disubstituted 1,2,3-triazole group.

In particular, as set out above, peptide compounds which are particularly advantageous according to the present invention are such that at least one amino acid is bonded to a unit capable of binding to serum albumin. It has been observed by the present inventors that, surprisingly, such a characteristic has the effect of very significantly increasing the duration of action of the peptide compound in the organism.

Preferentially, the unit capable of binding to serum albumin is attached to an amino acid located in the N-terminal region of the peptide compound.

An example of such a unit is a γ-(N-hexadecanoyl-L-glutamyl) group, also called γ-(N-hexadecanoyl-Glu-OH). It is in particular known from the prior art that the use of a γ-glutamyl spacer group, between the amino acid and a group capable of binding to serum albumin, such as a hexadecanoyl group (also called palmitoyl), increases the affinity of said group with serum albumin (Knudsen et al., 2000). Any other unit capable of binding to serum albumin, known in itself to those skilled in the art, may also be used in the context of the invention, for instance an ω-carboxylate fatty acid (Zarandi et al., 2006), Albu-tag (Dumelin et al., 2008) or a cyclopeptide (Dennis et al., 2002, Angelini et al., 2012). Examples of such units, and of the associated spacer arms for bonding thereof to a residue of the peptide compound according to the invention, are in particular TTDS-(γ-(N-hexadecanoyl-Glu-OH)) or else 2-(succinamido)-6-(4-(4-iodophenyl)butanamido)hexanoate.

When the peptide compound according to the invention is an analog of the pseudopeptide of sequence SEQ ID NO:4, preferably, a unit capable of binding to serum albumin is introduced at least at position 1, at position 2 and/or at position 3 of the peptide compound, i.e. at the level of Tyr1, Asn2 and/or Trp3, or residues which are analogous thereto. When the unit capable of binding serum albumin is attached at position 1, the unit is preferably attached to the N-terminal amine function. When the unit capable of binding serum albumin is attached at position 2 or 3 of the peptide compound, the residue concerned, for example the Asn2 residue, respectively the Trp3 residue, is preferably substituted with a lysine residue, on the side chain of which is attached the unit capable of binding to serum albumin.

Another aspect of the invention is the use of a peptide compound corresponding to one or more of the characteristics described above, as a medicament, and more particularly for inducing ovulation in a female mammal. This mammal may in particular be a livestock animal such as a member of the ovine race, a member of the goat family, a bovine, a pig, a member of the equine family, etc., a pet, such as a dog or a cat, or else, for example, a wild animal, such as is encountered in zoos and animal parks, etc.; aside from that, this mammal may be a human being.

More generally, the invention relates to the use of such a peptide compound for stimulating KISS1R, with a view to increasing GnRH secretion, and, consequently, for stimulating the release of the hormones LH and/or FSH in a mammal.

The peptide compound according to the invention may in particular be used in the context of the treatment of pathological states resulting from low circulating levels of LH and FSH, for example of pathological states resulting from insufficient pituitary gland stimulation. More generally, it may be used for the treatment of pathological conditions associated with a reduction in the activity of the hypothalamic-pituitary-gonadal axis, such as amenorrhea of hypothalamic origin or delayed puberty.

Other applications of the peptide compound according to the invention are in particular the treatment of certain forms of cancer, sensitive to steroid hormones, or else the delaying of aging by stimulation of GnRH secretion (Zhang et al., 2013).

The peptide compound according to the invention is preferably administered in injection form, it being possible for said injection to be carried out, for example, intramuscularly, intravenously, subcutaneously or intradermally. For example, the treatment may consist of a single injection of the compound given to the mammal to be treated.

The administration can also be carried out orally.

The dose of the peptide compound administered according to the invention may be between 1 µg and 1 mg, in particular between 1 µg and 250 µg, depending on the mammal and the molecular weight of the compound. For example, for a ewe, the dose administered may be approximately 10 µg.

According to another aspect, the present invention relates to a veterinary or pharmaceutical composition, in particular for inducing ovulation in a female mammal, which contains a peptide compound corresponding to one or more of the characteristics above, in a pharmaceutically acceptable carrier.

This composition is preferably in an intramuscularly, subcutaneously, intravenously or intradermally administrable form, or in an orally administrable form.

BRIEF DESCRIPTION OF THE DRAWINGS

The characteristics and advantages of the invention will emerge more clearly in the light of the exemplary embodiments hereinafter, provided as simple and in no way limiting illustration of the invention, with the support of FIGS. 1 to 10, in which:

FIG. 2a, compound C1; FIG. 2b, compound C2; FIG. 2c, compound C3; FIG. 2d, compound C4; FIG. 2e, compound C5; FIG. 2f, compound C6; FIG. 2g, compound C7; for the comparative compound Comp.2 in FIG. 2h; for the comparative compound Comp.3 in FIG. 2i; and, in all the figures, the comparative compound Comp.1;

FIG. 5a, compound C8; FIG. 5b, compound C9; FIG. 5c, compound C10; FIG. 5d, compound C11; FIG. 5e, compound C12; FIG. 5f, compound C13; FIG. 5g, compound C14; FIG. 5h, compound C15; FIG. 5i, compound C16; and, in all the figures, for the comparative compound Comp.1;

FIG. 6a, Comp.1; FIG. 6b, Comp.3; FIG. 6c, C1; FIG. 6d, C2;

FIG. 8a, C2; FIG. 8b, C8, in concentrations of 1 nmol/ewe, 5 nmol/ewe and 15 nmol/ewe;

Figure 1:
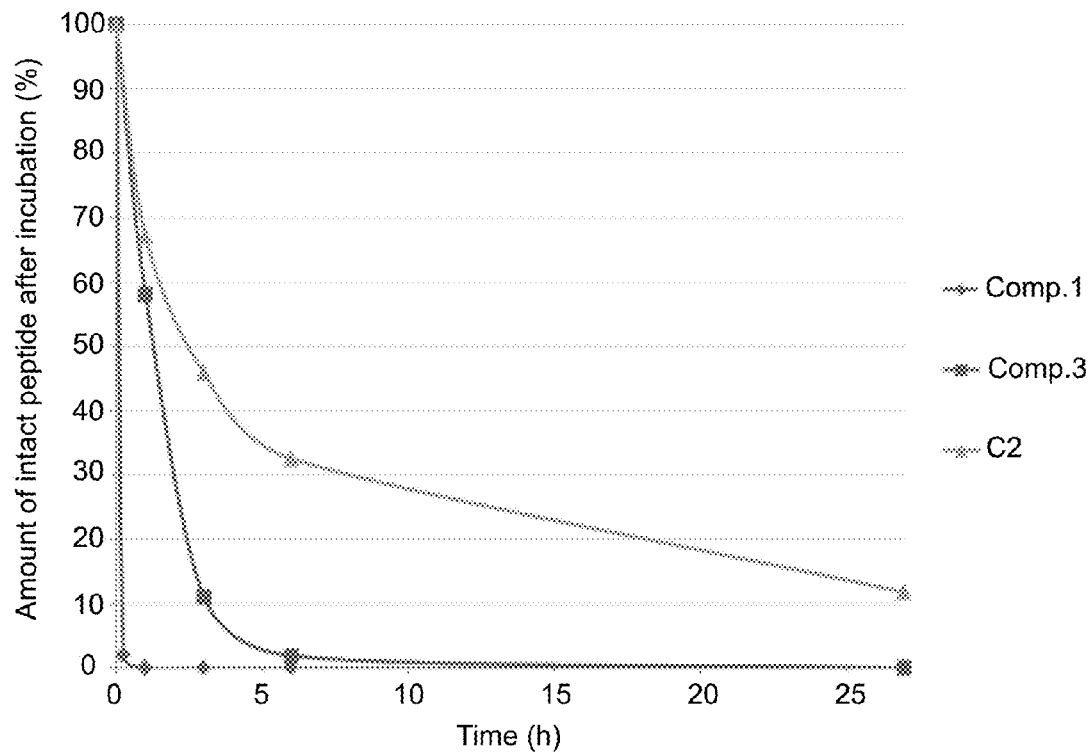
FIG. 1 is a graph showing, as a function of time, the amount of peptide remaining intact after incubation at 39° C. in ovine serum, for the peptide compound C2 in accordance with the invention and for the comparative compounds Comp.1 and Comp.3, this amount being expressed as % of the area of the HPLC peak at time t=0.

EXAMPLE 1—SYNTHESIS OF PEPTIDE COMPOUNDS IN ACCORDANCE WITH THE INVENTION 1.1/ General Procedure The peptide syntheses are carried out on solid phase using Fmoc/tBu strategy, at a scale of 0.1 nmol. The solid support used is a ChemMatrix® resin functionalized with a Rink amide arm.

The automated extension of the peptides is carried out using the Applied Biosystems 433A synthesizer. The Fastmoc® standard synthesis program supplied by the constructor is used with simple coupling followed by a step of acetylation with acetic anhydride after each coupling. The couplings are carried out using 10 equivalents of protected amino acid, 9.5 equivalents of HCTU (2-(6-chloro-1H-benzotriazol-1-yl)-1,1,3,3-tetramethylaminium hexafluorophosphate) and 20 equivalents of diisopropylethylamine in N-methyl-2-pyrrolidone (NMP). The Fmoc group is deprotected using a solution of 20% of piperidine in NMP. The side-chain protective groups used are Arg(Pbf), Arg(Me, Pbf), Asn(Trt), Ser(tBu), Trp(Boc), Tyr(tBu), Hyp(tBu) and Thr(tBu).

The pseudopeptide bonds of 1,4-disubstituted 1,2,3-triazole type (ψ[4-(1,2,3-triazol-1-yl)], abbreviated to ψ[Tz]) are formed by copper (I)-catalyzed azide-alkyne cycloaddition (CuAAC), in solution (route A) or on a solid support (route B), according to the general reaction schemes hereinafter:

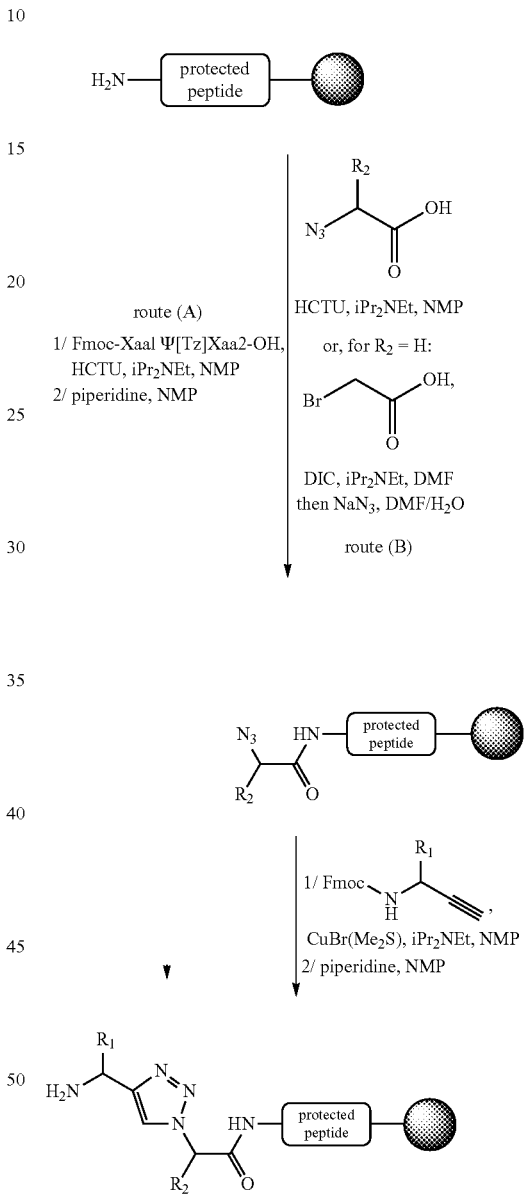

In the case of the introduction of several consecutive ψ[Tz] bonds, the formation of the first triazole is carried out on a solid support by cycloaddition with an N-Fmoc α-amino alkyne. The Fmoc group is then deprotected under standard conditions, then the amine is converted into azide using a diazo transfer reagent. The formation of the second triazole is then carried out by cycloaddition with an N-Fmoc α-amino alkyne, according to the general reaction scheme hereinafter (route C):

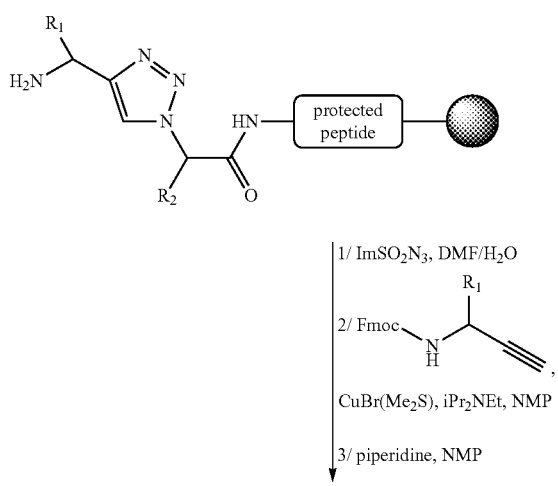

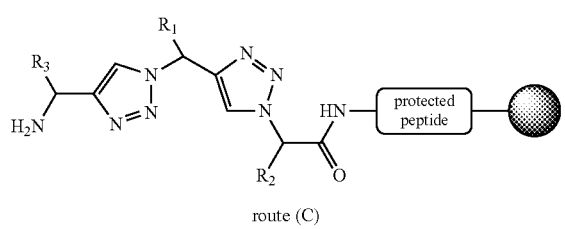

route (C)

The crude triazolopeptide is finally released from the resin with an 87.5/5/2.5/5 TFA/H₂O/iPr₃SiH/phenol solution for 2 h. The peptide is precipitated from cold Et₂O, centrifuged, and then washed three times with Et₂O.

It is then purified by RP-HPLC (nucleosil C18 300 Å column, 5 μm, 10×250 mm, 3 ml/min, eluent A=H₂O+0.1% TFA, eluent B=CH₃CN+0.1% TFA).

The pure triazolopeptide is analyzed by HPLC (using either a Nucleosil C18 300 Å column, 5 μm, 4.6×250 mm, 1 ml/min, or a Chromolith HighResolution RP-18 column, 4.6×100 mm, 3 ml/min) and MALDI-TOF mass spectrometry (matrix: α-cyano-4-hydroxycinnamic acid, instrument: Ultraflex, Bruker Daltonics, Germany). When nothing is specified in the description, the theoretical and experimental values given correspond to the monoisotopic ion.

1.2/ Synthesis Intermediates (S)-2-azido-4-methylpentanoic acid (1):

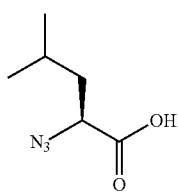

(1)

This compound is synthesized according to the protocol described in Goddard-Borger and Stick, 2007.

N-Fmoc-prop-2-ynylamine (2)

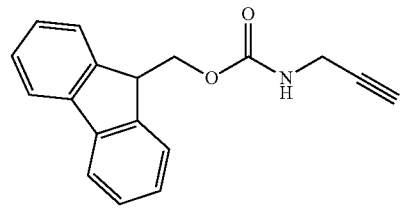

(2)

This compound is synthesized according to the protocol described in Pokorski et al., 2007.

(S)-1-phenylbut-3-yn-2-amine (3)

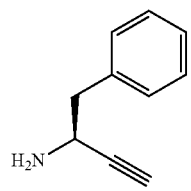

(3)

This compound is synthesized according to the protocol described in Reginato et al., 1996.

N-Fmoc-(S)-1-phenylbut-3-yn-2-amine (4)

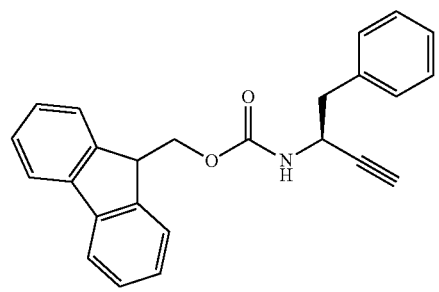

(4)

(S)-1-phenylbut-3-yn-2-amine (3) (1.45 g, 10 mmol, 1 eq.) and NaHCO₃ (1.3 g, 15 mmol, 1.5 eq.) are dissolved in a CH₃CN/H₂O mixture (1:1, 50 ml). After the addition of Fmoc-OSu (3.71 g, 11 mmol, 1.1 eq.), the solution is stirred for 16 h at ambient temperature. The reaction medium is then diluted with 100 ml of EtOAc. The organic phase is washed with an aqueous 1M NaHCO₃ solution (2×20 ml) then dried over MgSO₄ and concentrated under reduced pressure. The residue obtained is then purified by flash chromatography so as to obtain the compound (4) in the form of a white solid (3.2 g, 8.8 mmol, 88%).

¹H NMR (500 MHz, CDCl₃) δ=7.78 (d, J=7.6 Hz, 2H), 7.64-7.53 (m, 2H), 7.42 (t, J=7.5, 2H), 7.36-7.23 (m, 9H), 5.01-4.95 (m, 1H), 4.81-4.75 (m, 1H), 4.52-4.43 (m, 1H), 4.42-4.35 (m, 1H), 4.25-4.19 (m, 1H), 3.07-2.94 (m, 2H), 2.32 (d, J=2.4 Hz, 1H).

$^{13}$C NMR (125 MHz, CDCl$_3$) δ=155.39, 144.01, 141.55, 136.20, 130.04, 128.60, 127.95, 127.28, 125.28, 125.21, 120.22, 82.52, 72.88, 67.12, 47.43, 44.51, 41.68.

1.3/ Formation of the Triazole by CuAAC in Solution Fmoc-Glyψ[Tz]Leu-OH (5):

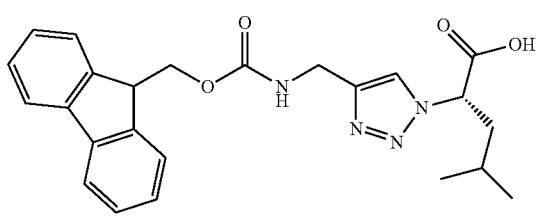

(5)

(S)-2-azido-4-methylpentanoic acid (1) (1.1 g, 7 mmol, 1 eq.) and N-Fmoc-prop-2-ynylamine (2) (2.0 g, 7.35 mmol, 1.05 eq.) are dissolved in a DMF/tBuOH/H$_2$O mixture (5:4:1, 36 ml) under an argon atmosphere. After the addition of iPr$_2$Net (1.2 ml, 7 mmol, 1 eq.) followed by CuBr(Me$_2$S) (144 mg, 0.7 mmol, 0.1 eq.), the reaction medium is stirred for 20 min at ambient temperature. The solution is then diluted with 150 ml of an aqueous 1M NaHCO$_3$ solution and then washed with Et$_2$O (2×20 ml). The aqueous phase is acidified with an aqueous 6M HCl solution to pH 2, and then extracted with EtOAc (4×50 ml). The organic phases are combined, dried over MgSO$_4$, and then concentrated on a rotary evaporator. The product (5) is obtained in the form of a pale green solid (3.01 g, 6.9 mmol, 98%), and is used as automated SPPS building block without an additional purification step.

$^1$H NMR (500 MHz, CDCl$_3$) δ=7.79-7.72 (m, 3H), 7.59-7.50 (m, 2H), 7.44-7.35 (m, 2H), 7.35-7.21 (m, 2H), 5.72-5.68 (s, 1H), 5.49-5.43 (m, 1H), 4.57-4.43 (m, 3H), 4.39-4.34 (m, 1H), 4.22-4.16 (m, 1H), 2.15-1.98 (m, 2H), 1.41-1.32 (m, 1H), 0.96 (d, J=6.4 Hz, 3H), 0.90 (d, J=6.6 Hz, 3H).

$^{13}$C NMR (125 MHz, CDCl$_3$) δ=171.76, 156.89, 143.96, 143.80, 141.46, 127.92, 127.26, 125.32, 125.07, 120.18, 67.40, 47.25, 41.58, 41.45, 36.14, 24.93, 22.80, 21.45.

1.4/ Formation of the Triazole by CuAAC on a Solid Support

According to the general mode of synthesis carried out, the alkyne compound (0.4 mmol, 4 eq.) and CuBr(Me$_2$S) (82 mg, 0.4 mmol, 4 eq.) are dissolved in 10 ml of NMP under an argon atmosphere. After the addition of iPr$_2$Net (70 µl, 0.4 mmol, 4 eq.), the solution is drawn into a syringe fitted with a polypropylene frit, and containing the resin carrying the azide peptide (0.1 mmol). The reaction medium is stirred for 2 h at ambient temperature. The resin is then washed successively with NMP (3×2 min), CH$_2$Cl$_2$ (2×2 min), 1M pyridinium chloride in 95:5 CH$_2$Cl$_2$/MeOH (2×2 min), CH$_2$Cl$_2$ (2×2 min) and then DMF (2×2 min). The rest of the extension is carried out by standard SPPS.

1.5/ Introduction of the γ-(N-hexadecanoyl-L-glutamyl) modification

Modification on the N-Terminal Residue

According to the general mode of synthesis carried out, the resin carrying the modified peptide provided with a non-protected N-terminal amine function (50 µmol) is coupled, after automated SPPS extension, with Fmoc-Glu-OtBu (10 equivalents of protected amino acid, 9.5 equivalents of HCTU and 20 equivalents of diisopropylethylamine in NMP). The deprotection of the Fmoc group is carried out using a solution of 20% of piperidine in NMP. Hexadecanoic acid is then coupled (10 equivalents of acid, 9.5 equivalents of HCTU and 20 equivalents of diisopropylethylamine in a 1:4 NMP/CH$_2$Cl$_2$ mixture).

The crude γ-(N-hexadecanoyl-L-glutamyl)-triazolopeptide is finally released from the resin with 5 ml of 87.5/5/2.5/5 TFA/H$_2$O/iPr$_3$SiH/phenol solution for 2 h. The resin is rinsed with TFA (2×5 ml for 5 min), and the filtrates are concentrated at ambient temperature using a rotary evaporator to a volume of approximately 1 ml. The peptide is precipitated by dilution with 40 ml of Et$_2$O precooled to −80° C., then centrifuged and washed twice with Et$_2$O. It is then purified and analyzed according to standard protocols.

Modification on the Side Chain of the Residue at Position 2 or 3

According to the general mode of synthesis carried out, a derivative of Fmoc-L-lysine provided with a Dde group on its side chain, Fmoc-Lys(Dde)-OH, is introduced at position 2 or 3 during the SPPS. After the automated synthesis, the resin carrying the modified peptide provided with an N-Dde amine function (50 µmol) is treated with 10 ml of a solution of hydrazine at 2% in NMP (2×5 min) in order to remove the Dde group, then the resin carrying the modified peptide provided with a non-protected amine function (50 µmol) is treated according to a protocol identical to that used for the introduction of the modification at position 1.

1.6/ Comparative Peptide Compound Comp.1 (mKP10)

The peptide compound Comp.1, of sequence SEQ ID NO:1:

H-Tyr-Asn-Trp-Asn-Ser-Phe-Gly-Leu-Arg-Tyr-NH$_2$, of chemical formula:

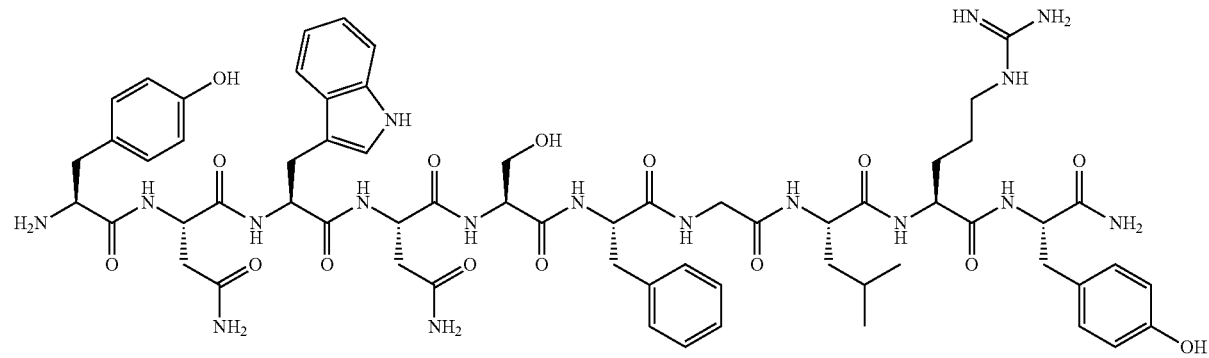 [SMILES: CC(C)C[C@H](NC(=O)CNC(=O)[C@H](Cc1ccccc1)NC(=O)[C@H](CO)NC(=O)[C@H](CC(N)=O)NC(=O)[C@H](Cc1c[nH]c2ccccc12)NC(=O)[C@H](CC(N)=O)NC(=O)[C@@H](N)Cc1ccc(O)cc1)C(=O)N[C@@H](CCCNC(=N)N)C(=O)N[C@@H](Cc1ccc(O)cc1)C(N)=O]

is prepared by standard SPPS.

HPLC (Nucleosil): $t_R$=19.2 min (gradient: 20-40% MeCN/$H_2O$+0.1% TFA in 30 min); detection UV ($\lambda$=280 nm); MS: m/z observed=1318.6 ([MH]+ calculated for $C_{63}H_{84}N_{17}O_{15}$=1318.6).

1.7/ Peptide Compound Comp.2 (hKP10)

The peptide compound Comp.2, of sequence SEQ ID NO:2:

H-Tyr-Asn-Trp-Asn-Ser-Phe-Gly-Leu-Arg-Phe-$NH_2$, of chemical formula:

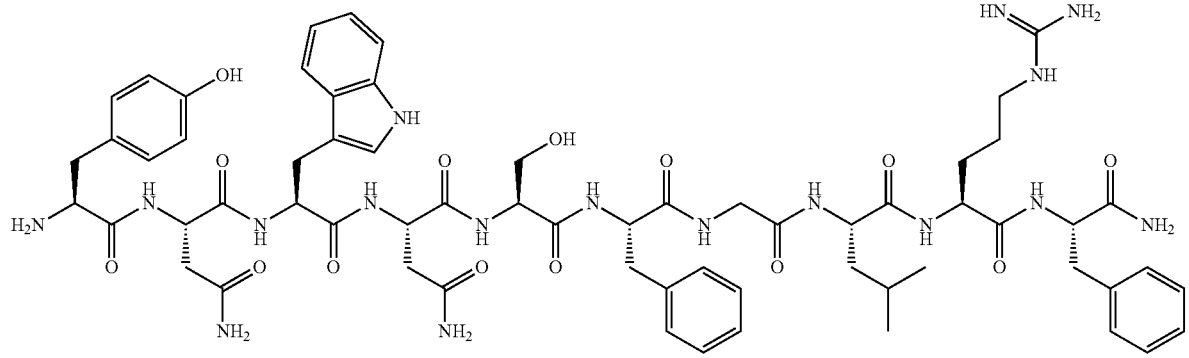 [SMILES: CC(C)C[C@H](NC(=O)CNC(=O)[C@H](Cc1ccccc1)NC(=O)[C@H](CO)NC(=O)[C@H](CC(N)=O)NC(=O)[C@H](Cc1c[nH]c2ccccc12)NC(=O)[C@H](CC(N)=O)NC(=O)[C@@H](N)Cc1ccc(O)cc1)C(=O)N[C@@H](CCCNC(=N)N)C(=O)N[C@@H](Cc1ccccc1)C(N)=O]

is obtained from the supplier Genecust (Dudelange, Luxembourg).

1.8/ Peptide Compound Comp.3

The peptide compound Comp.3, of sequence SEQ ID NO:10:

Ac-Tyr-Asn-Trp-Asn-Ser-Phe-Gly-Leu-Arg-Tyr-$NH_2$, corresponding to mKP10, in which the N-terminal end is modified by acetylation, and of chemical formula:

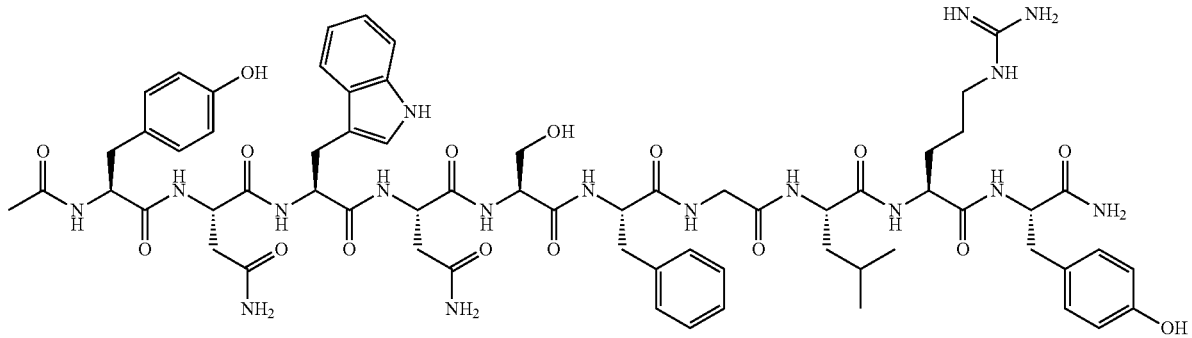 [SMILES: CC(=O)N[C@@H](Cc1ccc(O)cc1)C(=O)N[C@@H](CC(N)=O)C(=O)N[C@@H](Cc1c[nH]c2ccccc12)C(=O)N[C@@H](CC(N)=O)C(=O)N[C@@H](CO)C(=O)N[C@@H](Cc1ccccc1)C(=O)NCC(=O)N[C@@H](CC(C)C)C(=O)N[C@@H](CCCNC(=N)N)C(=O)N[C@@H](Cc1ccc(O)cc1)C(N)=O]

is prepared by standard SPPS.

HPLC (Nucleosil): $t_R$=21.9 min (gradient: 20-40% MeCN/$H_2O$+0.1% TFA in 30 min); detection UV ($\lambda$=280 nm); MS: m/z observed=1360.6 ([MH]+ calculated for $C_{64}H_{84}N_{19}O_{14}$=1360.6).

1.9/ Peptide Compound C1

The peptide compound C1, of sequence SEQ ID NO:5:

H-Tyr-Asn-Trp-Asn-Ser-Phe-Gly$\Psi$[Tz]Leu-Arg-Tyr-$NH_2$, of chemical formula:

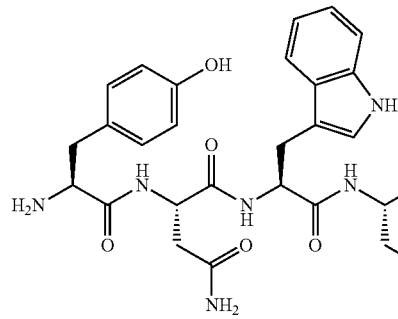
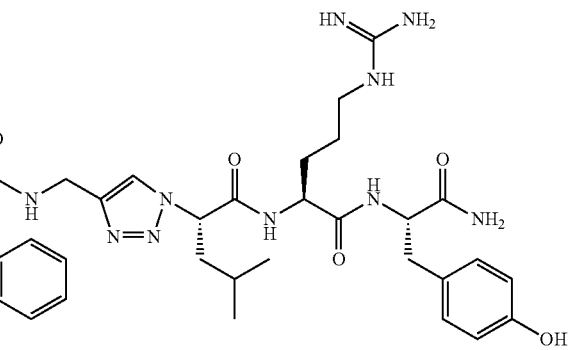

is prepared according to route B described above by introducing the azide function by automated coupling of the α-azido acid (1). The formation of the triazole by CuAAC on a solid support is carried out with the alkyne (2), according to the general procedure.

HPLC (Nucleosil): $t_R$=17.8 min (gradient: 20-40% MeCN/H$_2$O+0.1% TFA in 30 min); detection UV (λ=276 nm); MS: m/z observed=1341.6 ([MH]+ calculated for $C_{64}H_{84}N_{19}O_{14}$=1341.6).

1.10/ Peptide Compound C2

The peptide compound C2, of sequence SEQ ID NO:6:

Ac-Tyr-Asn-Trp-Asn-Ser-Phe-GlyΨ[Tz]Leu-Arg-Tyr-NH$_2$, of chemical formula:

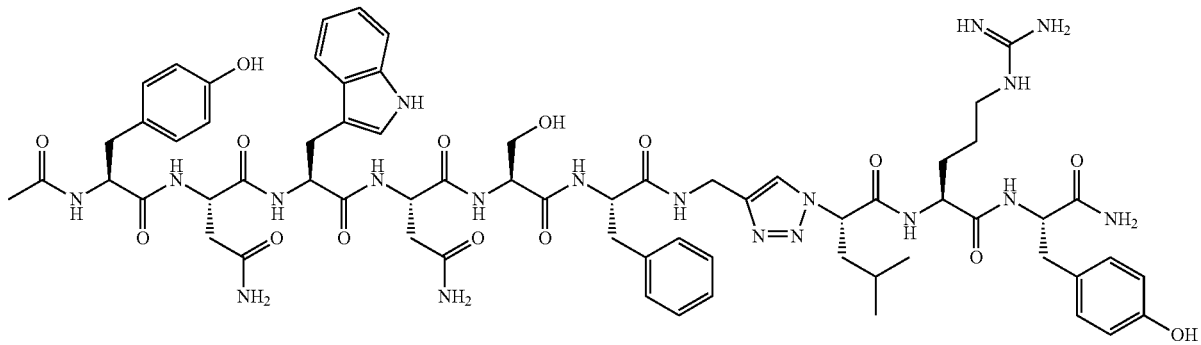 [SMILES: CC(=O)N[C@@H](Cc1ccc(O)cc1)C(=O)N[C@@H](CC(N)=O)C(=O)N[C@@H](Cc1c[nH]c2ccccc12)C(=O)N[C@@H](CC(N)=O)C(=O)N[C@@H](CO)C(=O)N[C@@H](Cc1ccccc1)C(=O)NCc1cn([C@@H](CC(C)C)C(=O)N[C@@H](CCCNC(=N)N)C(=O)N[C@@H](Cc2ccc(O)cc2)C(N)=O)nn1]

is prepared according to route B, by introducing the azide function by automated coupling of the α-azido acid (1). The formation of the triazole by CuAAC on a solid support is carried out with the alkyne (2), according to the general procedure. The rest of the synthesis is carried out by standard SPPS.

HPLC (Nucleosil): $t_R$=20.5 min (gradient: 20-40% MeCN/H$_2$O+0.1% TFA in 30 min); detection UV (λ=277 nm); MS: m/z observed=1384.7 ([MH]+ calculated for C$_{66}$H$_{86}$N$_{19}$O$_{15}$=1384.6).

1.11/ Peptide Compound C3

The peptide compound C3, of sequence SEQ ID NO:7:

Ac-Tyr-Asn-Trp-Asn-Ser-Phe-GlyΨ[Tz]Leu-Arg(Me)-Tyr-NH$_2$, of chemical formula:

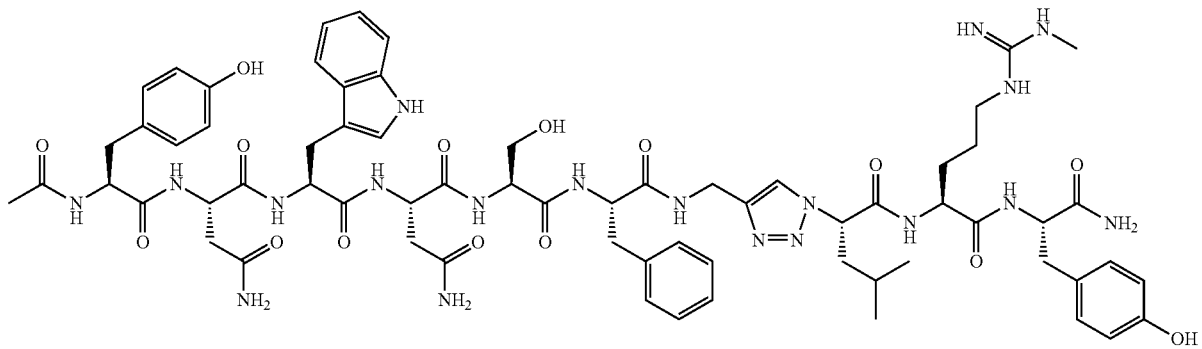 [SMILES: CNC(=N)NCCC[C@H](NC(=O)[C@H](CC(C)C)n1cc(CNC(=O)[C@H](Cc2ccccc2)NC(=O)[C@H](CO)NC(=O)[C@H](CC(N)=O)NC(=O)[C@H](Cc2c[nH]c3ccccc23)NC(=O)[C@H](CC(N)=O)NC(=O)[C@H](Cc2ccc(O)cc2)NC(C)=O)nn1)C(=O)N[C@@H](Cc1ccc(O)cc1)C(N)=O]

is prepared by introduction of the triazole according to route A, using the compound Fmoc-Glyψ[Tz]Leu-OH (5).

HPLC (Nucleosil): $t_R$=14.3 min (gradient: 25-40% MeCN/H$_2$O+0.1% TFA in 30 min); detection UV (λ=280 nm); MS: m/z observed=1398.7 ([MH]+ calculated for C$_{67}$H$_{88}$N$_{19}$O$_{15}$=1398.7).

1.12/ Peptide Compound C4

The peptide compound C4, of sequence SEQ ID NO:8:

Ac-Tyr-Asn-Lys(Ac)-Asn-Ser-Phe-GlyΨ[Tz]Leu-Arg(Me)-Tyr-NH$_2$, of chemical formula:

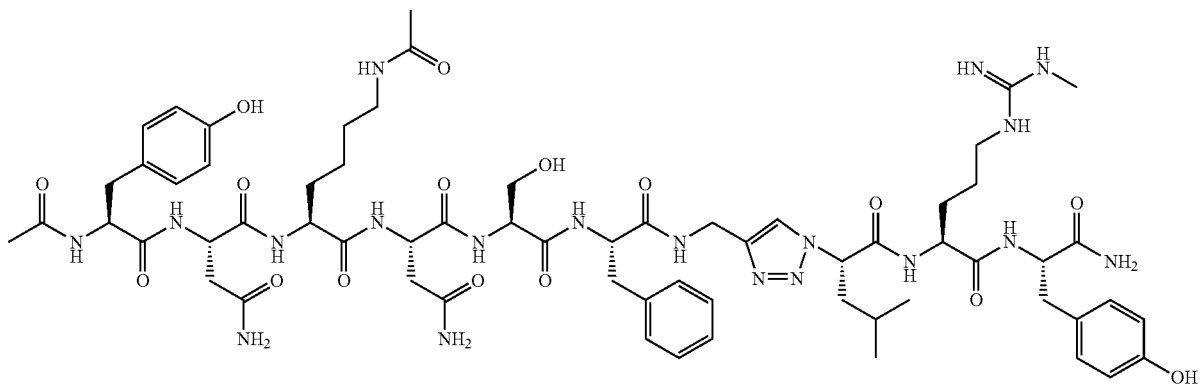 [SMILES: CNC(=N)NCCC[C@H](NC(=O)[C@H](CC(C)C)n1cc(CNC(=O)[C@H](Cc2ccccc2)NC(=O)[C@H](CO)NC(=O)[C@H](CC(N)=O)NC(=O)[C@H](CCCCNC(C)=O)NC(=O)[C@H](CC(N)=O)NC(=O)[C@H](Cc2ccc(O)cc2)NC(C)=O)nn1)C(=O)N[C@@H](Cc1ccc(O)cc1)C(N)=O]

is prepared by introduction of the triazole according to route A, using the compound Fmoc-Glyψ[Tz]Leu-OH (5).

HPLC (Nucleosil): $t_R$=12.9 min (gradient: 20-40% MeCN/H$_2$O+0.1% TFA in 30 min); detection UV (λ=280 nm); MS: m/z observed=1382.7 ([MH]+ calculated for $C_{64}H_{92}N_{19}O_{16}$=1382.7).

1.13/ Peptide Compound C5
The peptide compound C5, of sequence SEQ ID NO:9:

Ac-Tyr-Asn-Trp-Asn-Ser-PheΨ[Tz]GlyΨ[Tz]Leu-Arg-Tyr-NH$_2$, of chemical formula:

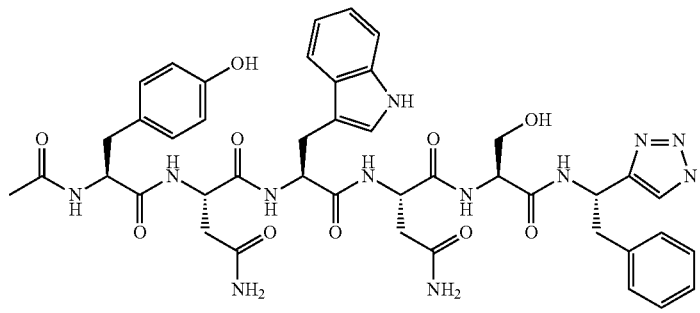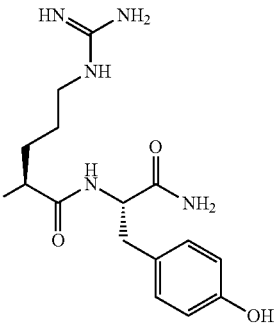

is prepared in the following way.

The first triazole (Glyψ[Tz]Leu) is formed according to route B, by introducing the azide function by automated coupling of the α-azido acid (1). The formation of the triazole by CuAAC on a solid support is carried out with the alkyne (2), according to the general procedure. The second triazole (Pheψ[Tz]Gly) is formed according to route C. After deprotection of the Fmoc group, the resin is stirred for 1 h with the diazo transfer reagent 1H-imidazole-sulfonyl azide.H$_2$SO$_4$ (135 mg, 0.5 mmol, 5 eq.), and K$_2$CO$_3$ (140 mg, 1 mmol, 10 eq.) dissolved in DMF/H$_2$O (3/7, 3 ml). After washing of the resin, the resulting supported azidopeptide is used in a CuAAC reaction on a solid support with the alkyne (4), according to the general procedure. The rest of the synthesis is carried out by standard SPPS.

HPLC (Nucleosil): $t_R$=15.9 min (gradient: 25-40% MeCN/H$_2$O+0.1% TFA in 30 min); detection UV (λ=280 nm); MS: m/z observed=1408.7 ([MH]+ calculated for $C_{60}H_{82}N_{17}O_{13}$=1408.7).

1.14/ Peptide Compound C6
The peptide compound C6, of sequence:

Ac-DTyr-DTrp-Asn-Thr-Phe-GlyΨ[Tz]Leu-Arg(Me)-Trp-NH$_2$, of chemical formula:

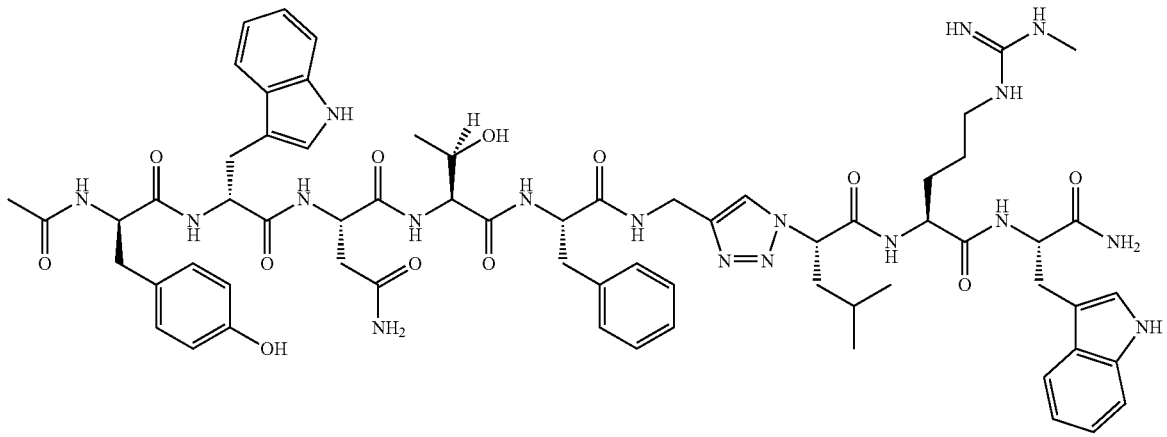 [SMILES: CNC(=N)NCCC[C@H](NC(=O)[C@H](CC(C)C)n1cc(CNC(=O)[C@H](Cc2ccccc2)NC(=O)[C@@H](NC(=O)[C@H](CC(N)=O)NC(=O)[C@@H](Cc2c[nH]c3ccccc23)NC(=O)[C@@H](Cc2ccc(O)cc2)NC(C)=O)[C@@H](C)O)nn1)C(=O)N[C@@H](Cc1c[nH]c2ccccc12)C(N)=O]

is prepared by introduction of the triazole according to route A, using the compound Fmoc-Glyψ[Tz]Leu-OH (5).

HPLC (Nucleosil): $t_R$=28.4 min (gradient: 20-40% MeCN/H$_2$O+0.1% TFA in 30 min); detection UV (λ=280 nm); MS: m/z observed=1321.7 ([MH]+ calculated for $C_{66}H_{85}N_{18}O_{12}$=1321.7).

1.15/ Peptide Compound C7

The peptide compound C7, of sequence:

Ac-D-Tyr-Hyp-Asn-Thr-Phe-GlyΨ[Tz]Leu-Arg(Me)-Trp-NH$_2$, of chemical formula:

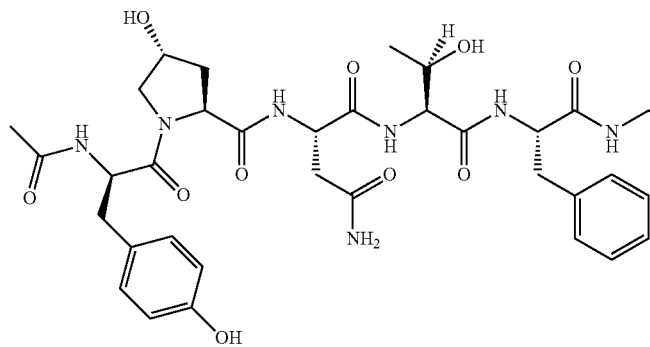

is prepared by introduction of the triazole according to route A described above, using the compound Fmoc-Glyψ[Tz]Leu-OH (5).

HPLC (Nucleosil): $t_R$=21.3 min (gradient: 20-40% MeCN/H$_2$O+0.1% TFA in 30 min); detection UV (λ=280 nm); MS: m/z observed=1248.6 ([MH]+ calculated for $C_{60}H_{82}N_{17}O_{13}$=1248.6).

1.16/ Peptide Compound C8

The peptide compound C8, of sequence SEQ ID NO:11:

Ac-Tyr-Lys(γ-(N-hexadecanoyl-Glu-OH))-Trp-Asn-Ser-Phe-GlyΨ[Tz]Leu-Arg-Tyr-NH$_2$, in which γ-(N-hexadecanoyl-Glu-OH) represents a unit of formula (II):

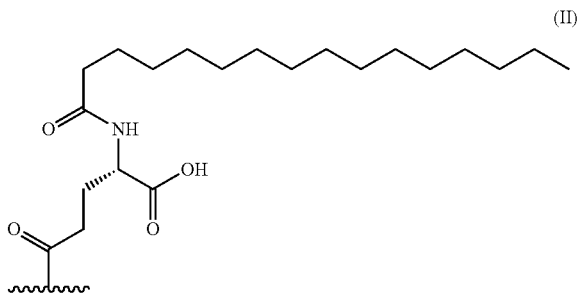

(II)

is prepared according to route B, by introducing the azide function by automated coupling of the α-azido acid (1). The formation of the triazole by CuAAC on a solid support is carried out with the alkyne (2), according to the general procedure. The remainder of the extension the synthesis is continued by standard SPPS, then the γ-(N-hexadecanoyl-Glu-OH) modification is introduced according to the general procedure for positions 2/3.

HPLC (Nucleosil): $t_R$=19.9 min (gradient: 45-75% MeCN/H$_2$O+0.1% TFA in 30 min); detection UV (λ=280 nm); MS: m/z observed=1766.0 ([MH]+ calculated for $C_{89}H_{128}N_{20}O_{18}$=1766.0).

1.17/ Peptide Compound C9

The peptide compound C9, of sequence SEQ ID NO:12:

γ-(N-hexadecanoyl-Glu-OH)-Tyr-Asn-Trp-Asn-Ser-Phe-GlyΨ[Tz]Leu-Arg-Tyr-NH$_2$, in which γ-(N-hexadecanoyl-Glu-OH) represents a unit of formula (II) above, is prepared according to route B, by introducing the azide function by automated coupling of the α-azido acid (1). The formation of the triazole by CuAAC on a solid support is carried out with the alkyne (2), according to the general procedure. The remainder of the extension the synthesis is continued by standard SPPS, then the γ-(N-hexadecanoyl-Glu-OH) modification is introduced according to the general procedure for position 1.

HPLC (Chromolith): $t_R$=6.15 min (gradient: 20-40% MeCN/H$_2$O+0.1% TFA in 6 min); detection UV (λ=280 nm); MS: m/z observed=1710.0 ([MH]+ calculated for $C_{85}H_{120}N_{20}O_{18}$=1710.0).

1.18/ Peptide Compound C10

The peptide compound C10, of sequence SEQ ID NO:13:

γ-(N-hexadecanoyl-Glu-OH)Tyr-Asn-Trp-Asn-Ser-Phe-GlyΨ[Tz]Leu-Arg-Trp-NH$_2$, in which γ-(N-hexadecanoyl-Glu-OH) represents a unit of formula (II) above, is prepared according to route B, by introducing the azide function by automated coupling of the α-azido acid (1). The formation of the triazole by CuAAC on a solid support is carried out with the alkyne (2), according to the general procedure. The remainder of the extension the synthesis is continued by standard SPPS, then the γ-(N-hexadecanoyl-Glu-OH) modification is introduced according to the general procedure for position 1.

HPLC (Chromolith): $t_R$=4.3 min (gradient: 45-75% MeCN/H$_2$O+0.1% TFA in 6 min); detection UV (λ=280 nm); MS: m/z observed=1732.9 ([MH]+ calculated for $C_{87}H_{121}N_{21}O_{17}$=1732.9).

1.19/ Peptide Compound C11

The peptide compound C11, of sequence SEQ ID NO:14:

Ac-Tyr-Asn-Lys(γ-(N-hexadecanoyl-Glu-OH))-Asn-Ser-Phe-GlyΨ[Tz]Leu-Arg-Tyr-NH$_2$, in which γ-(N-hexadecanoyl-Glu-OH) represents a unit of formula (II) above, is prepared according to route B, by introducing the azide function by automated coupling of the α-azido acid (1). The formation of the triazole by CuAAC on a solid support is carried out with the alkyne (2), according to the general procedure. The remainder of the extension the synthesis is continued by standard SPPS, then the γ-(N-hexadecanoyl-Glu-OH) modification is introduced according to the general procedure for positions 2/3.

HPLC (Chromolith): $t_R$=3.05 min (gradient: 45-75% MeCN/H$_2$O+0.1% TFA in 6 min); detection UV (λ=280 nm); MS: m/z observed=1693.9 ([MH]+ calculated for $C_{82}H_{124}N_{20}O_{19}$=1694.0).

1.20/ Peptide Compound C12

The peptide compound C12, of sequence SEQ ID NO:15:

γ-(N-hexadecanoyl-Glu-OH)Tyr-Asn-Trp-Asn-Ser-
Phe-GlyΨ[Tz]Leu-Arg(Me)-Tyr-NH$_2$, in which γ-(N-hexadecanoyl-Glu-OH) represents a unit of formula (II) above, is prepared according to route B, by introducing the azide function by automated coupling of the α-azido acid (1). The formation of the triazole by CuAAC on a solid support is carried out with the alkyne (2), according to the general procedure. The remainder of the elongation the synthesis is continued by standard SPPS, then the γ-(N-hexadecanoyl-Glu-OH) modification is introduced according to the general procedure for position 1.

HPLC (Chromolith): $t_R$=4.25 min (gradient: 45-75% MeCN/H$_2$O+0.1% TFA in 6 min); detection UV (λ=280 nm); MS: m/z observed=1693.9 ([MH]+ calculated for $C_{85}H_{120}N_{20}O_{17}$=1693.9).

1.22/ Peptide Compound C14

The peptide compound C14, of sequence SEQ ID NO:17:

Ac-Tyr-Lys(TTDS-(γ-(N-hexadecanoyl-Glu-OH)))-
Trp-Asn-Ser-Phe-GlyΨ[Tz]Leu-Arg-Tyr-NH$_2$, in which TTDS is a 1,13-diamino-4,7,10-trioxatridecan-succinic acid spacer arm and TTDS-(γ-(N-hexadecanoyl-Glu-OH)) represents a unit of formula (III):

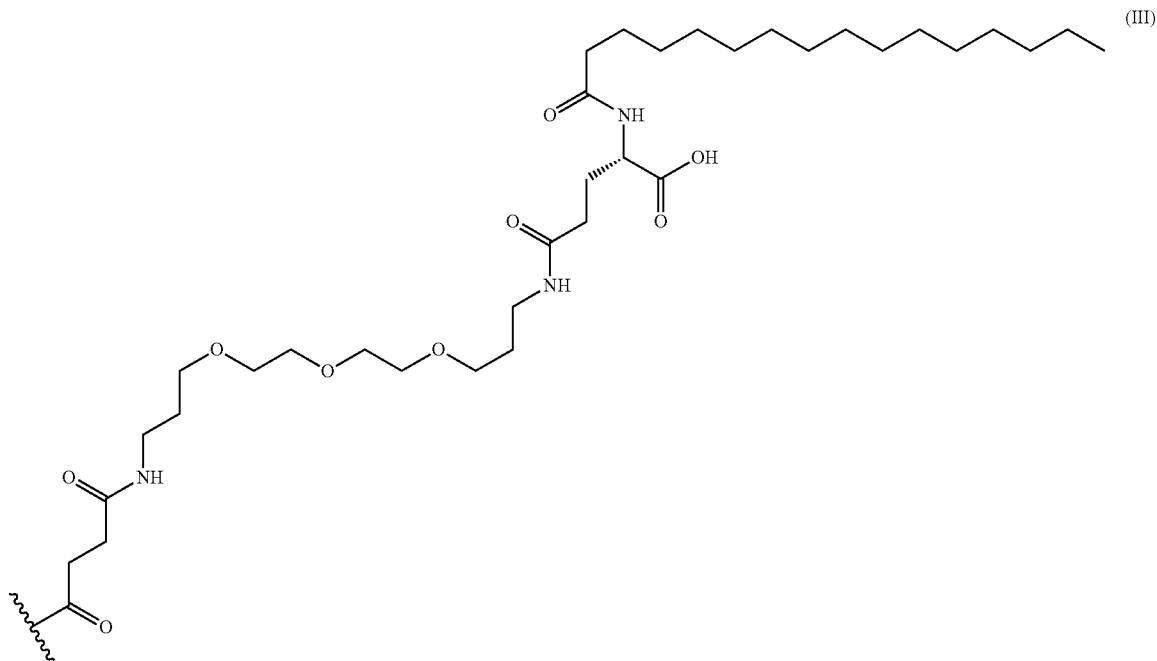

(III)

according to the general procedure. The remainder of extension the synthesis is continued by standard SPPS, then the γ-(N-hexadecanoyl-Glu-OH) modification is introduced according to the general procedure for position 1.

HPLC (Chromolith): $t_R$=3.8 min (gradient: 45-75% MeCN/H$_2$O+0.1% TFA in 6 min); detection UV (λ=280 nm); MS: m/z observed=1723.9 ([MH]+ calculated for $C_{86}H_{122}N_{20}O_{18}$=1723.9).

1.21/ Peptide Compound C13

The peptide compound C13, of sequence SEQ ID NO:16:

γ-(N-hexadecanoyl-Glu-OH)Tyr-Asn-Trp-Asn-Ser-
Phe-GlyΨ[Tz]Leu-Arg-Phe-NH$_2$, in which γ-(N-hexadecanoyl-Glu-OH) represents a unit of formula (II) above, is prepared according to route B, by introducing the azide function by automated coupling of the α-azido acid (1). The formation of the triazole by CuAAC on a solid support is carried out with the alkyne (2), is prepared according to route B, by introducing the azide function by automated coupling of the α-azido acid (1). The formation of the triazole by CuAAC on a solid support is carried out with the alkyne (2), according to the general procedure. The remainder of the extension is continued by SPPS using Fmoc-Lys(Dde)-OH for position 2. After the automated synthesis, the resin carrying the modified peptide provided with an N-Dde amine function (50 μmol) is treated with 10 ml of a solution of hydrazine at 2% in NMP (2×5 min) so as to remove the Dde group, then the resin carrying the modified peptide provided with a non-protected amine function (50 μmol) is coupled with [1-N-(9-fluorenyl-methoxycarbonyl)-1,13-diamino-4,7,10-trioxatridecan-suc-cinamic] acid (Fmoc-TTDS-OH, 3 equivalents, 3 equivalents of HATU (2-(7-aza-1H-benzotriazol-1-yl)-1,1,3,3-tetramethylaminium hexafluorophosphate) and 6 equivalents of diisopropylethylamine in NMP). The Fmoc group is removed by treatment with a solution of 20% of piperidine in NMP. Fmoc-Glu-OtBu is then coupled (10 equivalents of protected amino acid, 9.5 equivalents of HCTU and 20 equivalents of diisopropylethylamine in NMP). The deprotection of the Fmoc group is carried out using a solution of 20% piperidine in NMP. Hecadecanoic acid is then coupled (10 equivalents of acid, 9.5 equivalents of HCTU and 20 equivalents of diisopropylethylamine in a 1:4 NMP/CH$_2$Cl$_2$ mixture).

The crude TTDS-[γ-(N-hexadecanoyl-L-glutamyl)]-triazolopeptide is finally released from the resin with 5 ml of a solution of 87.5/5/2.5/5 TFA/H$_2$O/iPr$_3$SiH/phenol for 2 h. The resin is rinsed with TFA (2×5 ml for 5 min), and the filtrates are concentrated at ambient temperature using a rotary evaporator to a volume of approximately 1 ml. The peptide is precipitated by dilution with 40 ml of Et$_2$O precooled to −80° C., then centrifuged and washed twice with Et$_2$O. It is then purified and analyzed according to standard protocols.

HPLC (Chromolith): t$_R$=3.65 min (gradient: 45-75% MeCN/H$_2$O+0.1% TFA in 6 min); detection UV (λ=280 nm); MS: m/z observed=2068.2 ([MH]+ calculated for C$_{103}$H$_{154}$N$_{22}$O$_{23}$=2068.2).

1.23/ Peptide Compound C15
The peptide compound C15, of sequence SEQ ID NO:18:

Ac-Tyr-Lys[2-(succinamido)-6-(4-(4-iodophenyl)bu-
tanamido)hexanoate]-Trp-Asn-Ser-Phe-GlyΨ
[Tz]Leu-Arg-Tyr-NH$_2$, in which 2-(succinamido)-6-(4-(4-iodophenyl)butanamido)hexanoate represents a unit of formula (IV):

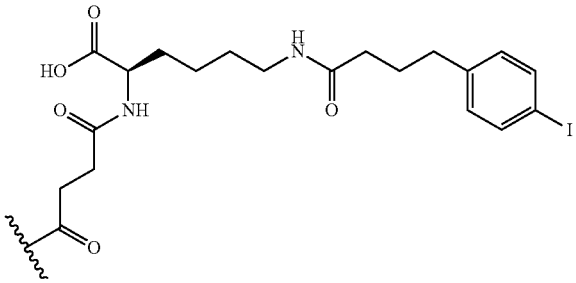

(IV)

is prepared according to route B, by introducing the azide function by automated coupling of the α-azido acid (1). The formation of the triazole by CuAAC on a solid support is carried out with the alkyne (2), according to the general procedure. The remainder of the extension is continued by SPPS using Fmoc-Lys(Dde)-OH for position 2. After the automated synthesis, the resin carrying the modified peptide provided with an N-Dde amine function (50 μmol) is treated with 10 ml of a solution of hydrazine at 2% in NMP (2×5 min) in order to remove the Dde group, then the resin carrying the modified peptide provided with a non-protected amine function (50 μmol) is treated with succinic anhydride (10 equivalents of anhydride and 20 equivalents of diisopropylethylamine in NMP). H-D-Lys(Boc)-OtBu is then coupled (10 equivalents of protected amino acid, 10 equivalents of PyAOP ((7-azabenzotriazol-1-yloxy)tripyrrolidinophosphonium hexafluorophosphate) and 20 equivalents of diisopropylethylamine in NMP). The crude triazolopeptide is finally released from the resin with 5 ml of a solution of 87.5/5/2.5/5 TFA/H$_2$O/iPr$_3$SiH/phenol for 2 h. The resin is rinsed with TFA (2×5 ml for 5 minutes), and the filtrates are concentrated at ambient temperature using a rotary evaporator to a volume of approximately 1 ml. The peptide is precipitated by dilution with 40 ml of Et$_2$O precooled to 0° C., then centrifuged and washed twice with Et$_2$O.

The peptide is finally coupled in solution with 4-(p-iodophenyl)butanoic acid (3 equivalents) activated in the form of its N-hydroxysuccinimide ester as described in the publication by Trüssel et al., 2009. The resulting compound C15 is then purified and analyzed according to standard protocols.

HPLC (Chromolith): t$_R$=4.85 min (gradient: 20-40% MeCN/H$_2$O+0.1% TFA in 6 min); detection UV (λ=280 nm); MS: m/z observed=1898.8 ([MH]+ calculated for C$_{88}$H$_{116}$IN$_{21}$O$_{19}$=1898.8).

1.24/ Peptide Compound C16
The peptide compound C16, of sequence SEQ ID NO:19:

Ac-Tyr-Lys(PEG5000)-Trp-Asn-Ser-Phe-GlyΨ[Tz]
Leu-Arg-Tyr-NH$_2$, in which PEG5000 represents a unit of formula COCH$_2$CH$_2$NH(CH$_2$CH$_2$O)$_n$Me with ~85<n<~130, having an average molecular weight of approximately 5000 g/mol, is prepared according to route B, by introducing the azide function by automated coupling of the α-azido acid (1). The formation of the triazole by CuAAC on a solid support is carried out with the alkyne (2), according to the general procedure. The remainder of the extension is continued by SPPS, using Fmoc-Lys(Boc)-OH for position 2. After the automated synthesis, the triazolopeptide (50 μmol) is finally released from the resin with 5 ml of a solution of 87.5/5/2.5/5 TFA/H$_2$O/iPr$_3$SiH/phenol for 2 h. The resin is rinsed with TFA (2×5 ml for 5 min), and the filtrates are concentrated at ambient temperature using a rotary evaporator to a volume of approximately 1 ml. The peptide is precipitated by dilution with 40 ml of Et$_2$O precooled to −80° C., then centrifuged and washed twice with Et$_2$O.

The peptide (2 equivalents) is finally coupled in solution with a commercial polymer (IRIS Biotech Gmbh) having an average weight of approximately 5000 g/mol, activated in the form of its N-hydroxysuccinimide ester (5 mM peptide in a mixture of 50 mM HEPES buffer, pH 8.5, and of MeCN, 9:1). The resulting compound C16 is then purified and analyzed according to standard protocols.

HPLC (Nucleosil): t$_R$=15-17 min (gradient: 35-55% MeCN/H$_2$O+0.1% TFA in 40 min); detection UV (λ=280 nm); MS: m/z observed=6182.2 ([MH]+ calculated for n=106, C$_{285}$H$_{522}$N$_{20}$O$_{122}$=6182.4, average weight, not monoisotopic).

EXAMPLE 2—TEST FOR PROTEOLYTIC DEGRADATION OF THE PEPTIDE COMPOUNDS IN OVINE SERUM

In order to carry out this test, blood was collected from the jugular vein of ewes of the Ile de France breed, and centrifuged. The supernatant (serum) was stored at −20° C. until use.

The degradation in this serum of the various peptide compounds in accordance with the invention and of the comparative peptide compounds is monitored over time. To this effect, each peptide compound to be analyzed and the internal calibrant (L-phenylalaninol) are dissolved in milliQ water (0.5 mM and 6.6 mM, respectively). The commercial protease inhibitor cocktail (Sigma, ref. P8340) is supplied in solution in DMSO.

The serum and the stock solutions of peptide compounds are preheated at 39° C. for 30 minutes. Each solution of peptide compound (50 μl, i.e. a final concentration in the serum of 50 μM) and the solution of internal calibrant (25 μl) are mixed with 425 μl of serum and incubated at 39° C. The proteolytic degradation kinetics of the compounds are monitored by taking a sample, at various given times, of 75 μl of the solution, which are diluted with 150 μL of acetonitrile in order to precipitate the serum proteins. The suspension obtained is centrifuged at 14 000 revolutions/min for 10 min at 4° C. 100 μl of the supernatant are diluted in 900 μl of a solution of TFA at 0.1% in water, then injected into HPLC for analysis (column: Chromolith® HighResolution RP-18 endcapped, 3 ml/min, gradient: 2-52% MeCN/H$_2$O+0.1% TFA in 5 min, UV detection, λ=214 nm).

The amount of peptide compound intact after incubation is determined by integration of the area of the peak, using L-phenylalaninol as internal calibrant. It is expressed as % of the area of the peak at time t=0.

The value corresponding to 100% of intact peptide compound is obtained by mixing 420 μl of serum, 5 μl of the inhibitor cocktail and 25 μl of the phenylalaninol solution, followed by 50 μl of peptide compound, and then by immediately treating the resulting solution according to the protocol described above. For all the compounds tested, the results obtained, after 3 h of incubation in the serum, are shown in table 1 below.

TABLE 1

Amounts of the intact peptide compounds after 3 h of incubation in ovine serum, expressed as % of the area of the HPLC peak at time t = 0

| Compound | % of peptide intact after 3 h of incubation in the serum |
|---|---|
| Comp. 1 | <0.1 |
| Comp. 2 | <0.1 |
| Comp. 3 | 11 |
| C2 | 46 |
| C3 | 55 |
| C4 | 59 |
| C5 | 51 |
| C6 | 50 |
| C7 | 17 |

These results demonstrate that the compounds in accordance with the invention C2 to C7 all have a lifetime in the ovine serum which is very greatly extended compared with the comparative natural compounds mKP10 (Comp.1) and hKP10 (Comp.2).

The advantage, in terms of extension of the half-life in ovine serum, of the replacement, with a triazole bond, of the amide bond between the glycine residue and the leucine residue is, in addition, clearly demonstrated by comparison of the kinetics of degradation in the serum that are obtained for the compound in accordance with the invention C2, and the comparative compound Comp.3, the structures of which differ only by virtue of the nature of said bond. In particular, these compounds both have an N-terminal N-acetyl group. These kinetics of proteolytic degradation in the ovine serum are illustrated in FIG. 1. It clearly emerges from this figure that the peptide compound in accordance with the invention C2 has a lifetime that is clearly prolonged in comparison with that of the comparative peptide compound Comp.3.

EXAMPLE 3—INTRACELLULAR CALCIUM MOBILIZATION TESTS 3.1/ Materials and Methods

In order to carry out the in vitro tests for the activity of the peptide compounds in accordance with the invention and the comparative compounds, the HEK293A cell line (ATCC, American Type Culture Collection, Manassas, Va., USA) was stably transfected with the human KISS1R receptor (Genbank accession number: NM_032551). The pcDNA3.1 vector (Invitrogen, Cergy Pontoise, France), into which the sequence of human KISS1R has been inserted with a 5' HA tag at position 957-2150 bp, was used for the transfection. The transfection and the selection of the clones were carried out as described in the literature (Mancini et al. 2009, and Invitrogen website).

The KISS1R receptor is coupled to Gq proteins and its activation produces an increase in intracellular calcium concentration. In order to verify the agonist activity and to measure the EC$_{50}$ of the peptide compounds according to the invention, the following protocol was carried out.

HEK293A cells expressing the human KISS1R receptor were seeded into a 96-well plate (μClear® black plate) at the concentration of 40 000 cells/well, and placed in an incubator at 37° C. After 48 hours, the medium was changed and the cells were incubated with the fluorescent dye Fluo-4NW, according to the instructions of the manufacturer (Molecular Probe).

In order to avoid adhesion of the peptide to the plastic, the test compounds were prediluted in a "non-binding" plate (Corning), to a concentration 20 times greater (20×) than the desired final concentration.

After having measured the basal fluorescence, 5 μl of the 20× solution containing the test compound were added to each well (containing 95 μl) so as to obtain the desired concentration. The variations in fluorescence were recorded every 7 seconds for 5-7 minutes with a plate reader (PolarStar Optima, BMG Labtech). Activity-concentration curves were generated using the GraphPad Prism 5 software, and the EC$_{50}$ of each compound was calculated by adjusting the curve to a sigmoid.

3.2/ Compounds C1 to C7 According to the Invention

Figure 2A:
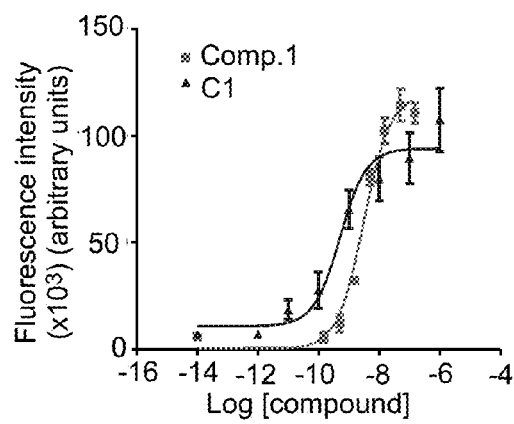
FIGS. 2a to 2i are graphs showing the fluorescence intensity, in arbitrary units, as a function of the concentration of compound, obtained in an intercellular calcium mobilization test attesting to the activation of KISS1R by the compound, for the following compounds in accordance with the invention.
Figure 2B:
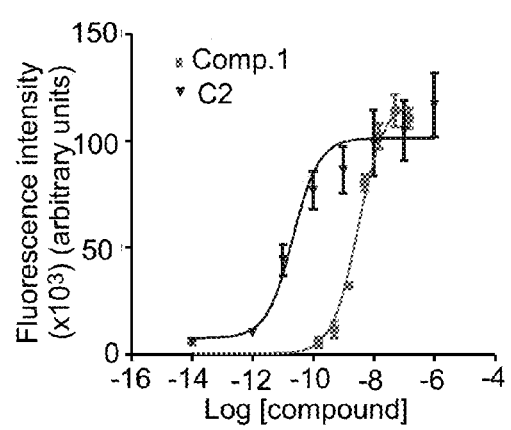
Figure 2C:
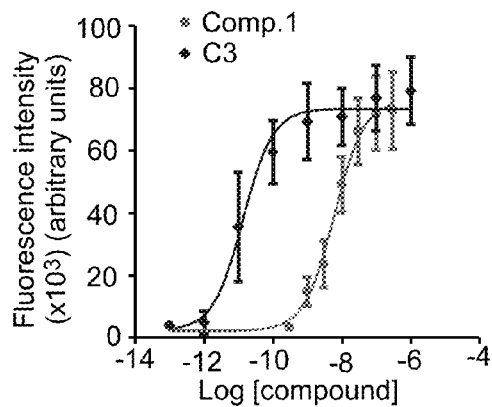
Figure 2D:
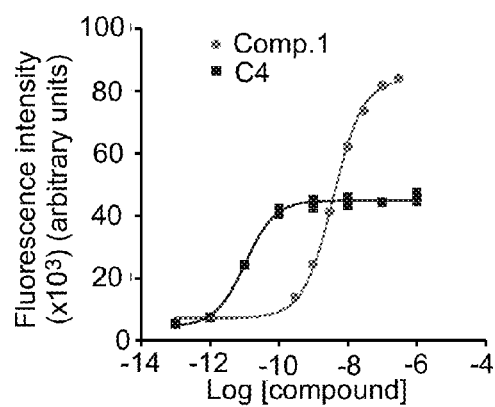
Figure 2E:
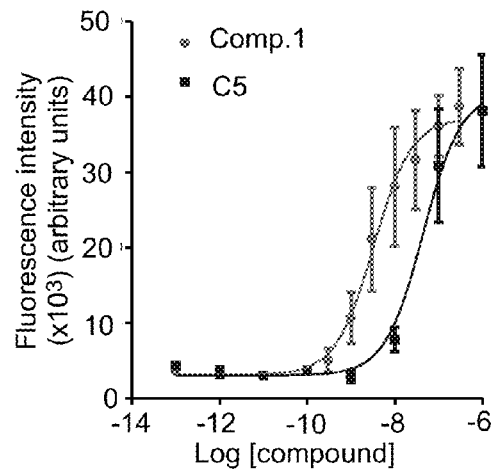
Figure 2F:
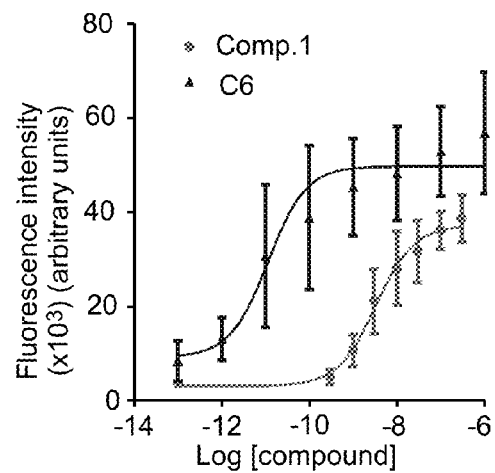
Figure 2G:
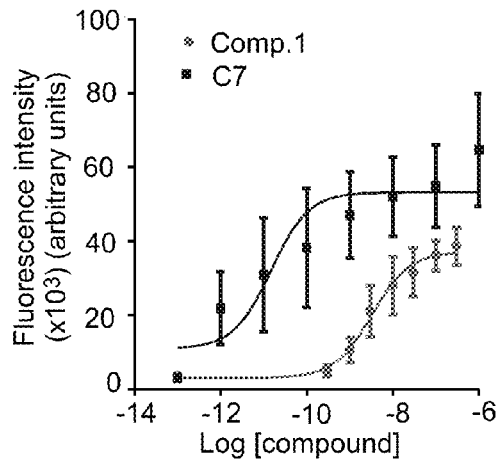
Figure 2H:
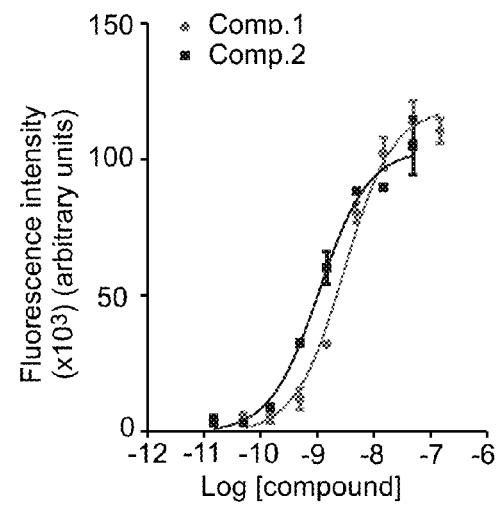
Figure 2I:
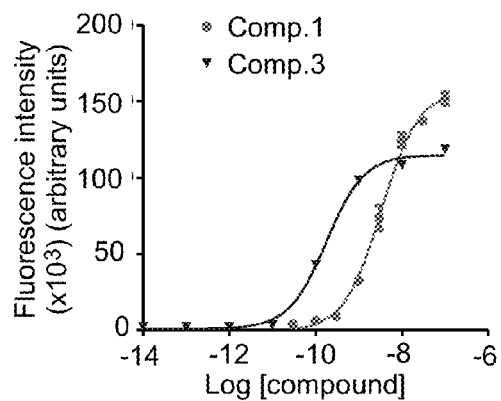

The curves obtained are shown in FIGS. 2a to 2g, respectively for the compounds in accordance with the invention C1, C2, C3, C4, C5, C6 and C7, in FIG. 2h for the comparative compound Comp.2 and in FIG. 2i for the comparative compound Comp.3. In each of these figures, the curve obtained for the comparative compound Comp.1 is also represented by way of comparison. The results obtained, in terms of EC$_{50}$, are shown in table 2 below.

TABLE 2

Effect of the peptide compounds on the intracellular calcium mobilization of cells expressing human KISS1R

| Compound | EC$_{50}$ (nM) |
|---|---|
| Comp. 1 | 2.9 |
| Comp. 2 | 0.8 |
| Comp. 3 | 0.1 |
| C1 | 0.5 |
| C2 | 0.029 |
| C3 | 0.014 |
| C4 | 0.011 |
| C5 | 44 |
| C6 | 0.01 |
| C7 | 0.014 |

These results show that the insertion of a disubstituted 1,2,3-triazole heterocycle as a replacement for the peptide bond between the glycine and the leucine, in accordance with the invention, increases the human KISS1R-stimulating power of the peptide compounds, with the exception of the compound C5, which remains, however, active, although to a lesser degree.

3.3/ Compounds C8 to C16 According to the Invention

The curves obtained are shown in FIGS. 5a to 5i, respectively for the compounds in accordance with the invention C8, C9, C10, C11, C12, C13, C14, C15 and C16. In each figure, the curve corresponding to the compound Comp.1, which was tested in parallel with each compound, is also represented. The results obtained, in terms of $EC_{50}$, are shown in table 3 below.

TABLE 3

Effect of the peptide compounds according to the invention, modified with a unit capable of binding to serum albumin (C8 to C15) or with a PEG (C16), on the intracellular calcium mobilization of cells expressing human KISS1R.

| Compound | $EC_{50}$ (nM) |
|---|---|
| C8 | 1.38 |
| C9 | <0.001 |
| C10 | <0.001 |
| C11 | 90 |
| C12 | <0.001 |
| C13 | 0.01 |
| C14 | 0.079 |
| C15 | 0.001 |
| C16 | 4.17 |

These results show that the insertion of a disubstituted 1,2,3-triazole heterocycle as a replacement for the peptide bond between the glycine and the leucine, combined with the presence, on the peptide compound, of a unit capable of binding to serum albumin, or PEG, in accordance with particular embodiments of the present invention, increases the human KISS1R-stimulating power of the peptide compounds, with the exception of the compound C11, which remains, however, active, although to a lesser degree, and of the compound C16, which shows a power similar to the comparative compound Comp.1.

EXAMPLE 4—IN VIVO ACTIVITY TESTS 4.1/ $1^{st}$ Experiment

In this example, the compounds in accordance with the invention C1, C4 and C6 and the comparative compound Comp.1 were tested.

The tests were carried out on ewes of the Ile de France breed, either in the anestrus period for the comparative compounds Comp.1 and Comp.3, or in the estrus period for the comparative compound Comp.1 and for the compounds in accordance with the invention C1, C4 and C6. The ewes used in the estrus period were pretreated with a vaginal sponge containing 20 mg of fluorogestone acetate (Chronogest CR sponge, Intervet) in order to block the secretion of LH and to stimulate a luteal phase.

Five days after the insertion of the sponge (for the animals in the estrus period) or the day before the test (for the animals in the anestrus period), a catheter was inserted into the jugular vein of the animal. On the day of the test, the peptide compound to be tested was injected into the catheter, at the desired dose (5 nmol/ewe), diluted in 1 ml of physiological solution. Physiological saline containing heparin (3 ml) was injected immediately after the peptide compound in order to rinse the catheter and to carry all of the compound into the animal's bloodstream.

A negative control (T) consisting of physiological solution alone was also carried out.

Before and following the injection of the test compound, blood samples were taken at variable intervals between 10 min and 1 h, for a period of between 3 h and 30 h.

The blood samples were centrifuged, and the plasma was stored at −20° C. until it was used to measure the LH concentration, according to an RIA method described in the literature (Caraty et al., 2007).

Figure 3:
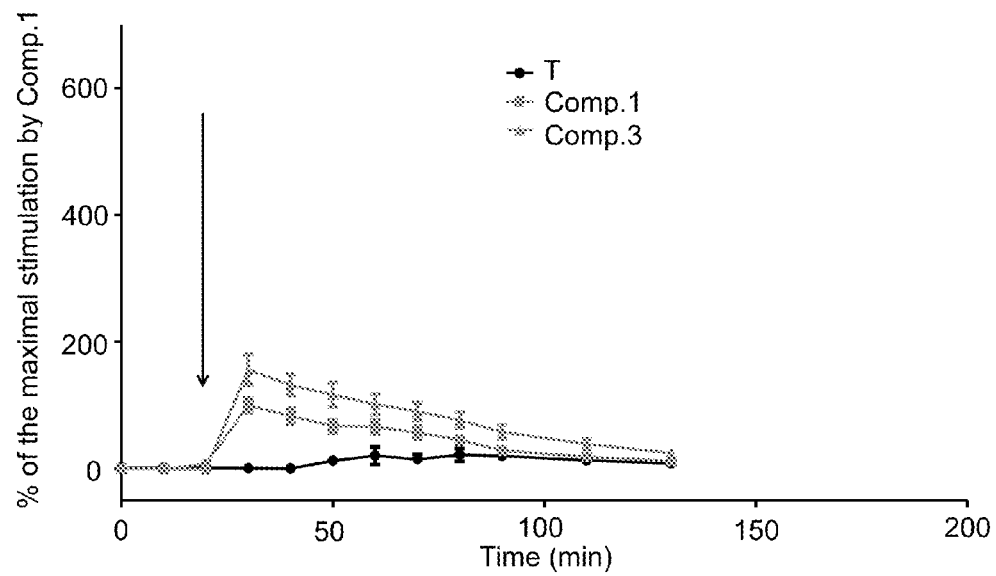
FIG. 3 shows the concentration of LH measured in blood samples taken from ewes in the anestrus period, at various times before and after the intravenous administration of physiological solutions containing, respectively, 5 nmol/ewe of the compounds Comp.1 or Comp.3, and of physiological solution alone (T), the moment of the administration being indicated by an arrow on the figure; said concentration of LH being expressed as percentage relative to the maximum concentration of LH measured after injection of 5 nmol/ewe of Comp.1 taken as reference (% of the maximum stimulation of Comp.1)
Figure 4:
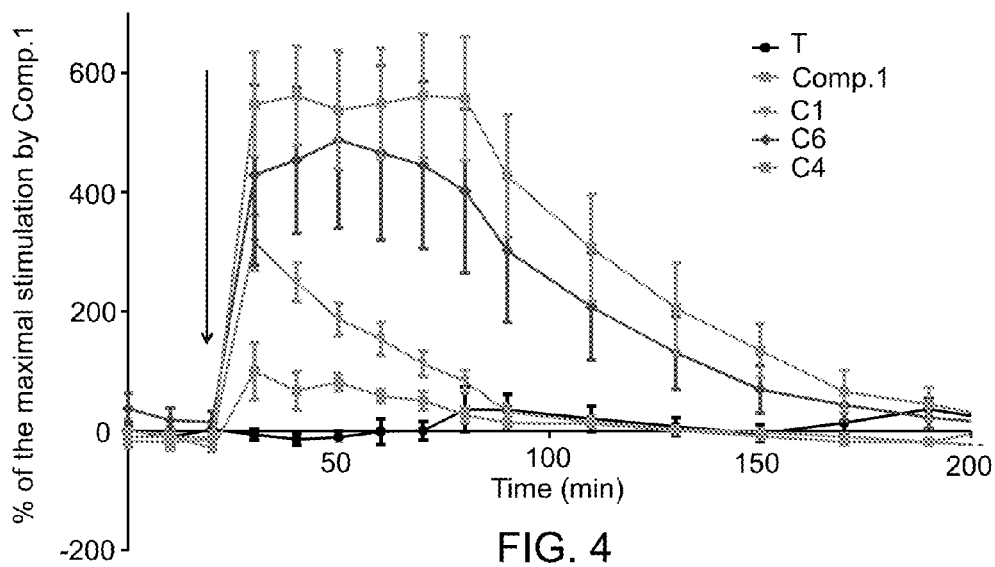
FIG. 4 shows the concentration of LH measured in blood samples taken from ewes in the estrus period, at various times before and after the intravenous administration of physiological solutions containing, respectively, 5 nmol/ewe of the comparative compound Comp.1, of the compounds in accordance with the invention C1, C4 and C6, and of physiological solution alone (T), the moment of the administration being indicated by an arrow on the figure; said concentration of LH being expressed as percentage relative to the maximum concentration of LH measured after injection of 5 nmol/ewe of Comp.1 taken as a reference (% of the maximum stimulation of Comp.1)
Figure 5A:
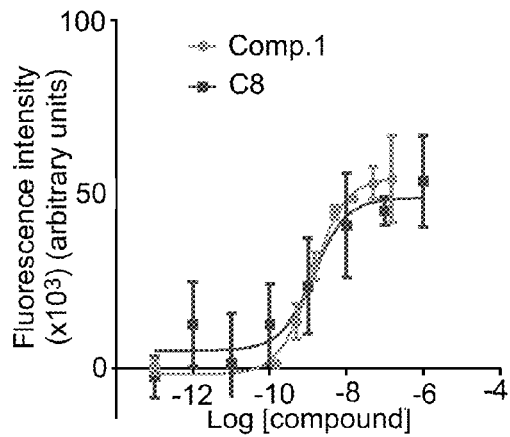
FIGS. 5a to 5i are graphs showing the fluorescence intensity, in arbitrary units, as a function of the concentration of compound, obtained in an intracellular calcium mobilization test attesting to the activation of KISS1R by the compound, for the following compounds in accordance with the invention.
Figure 5B:
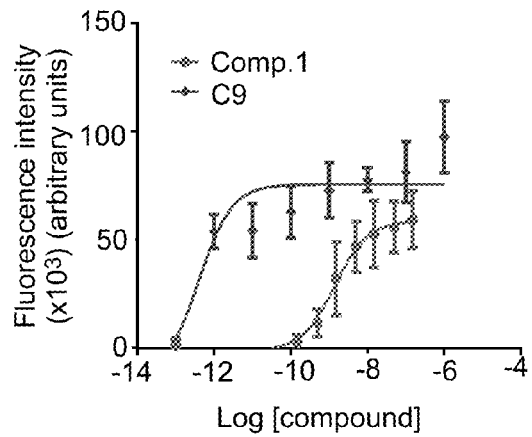
Figure 5C:
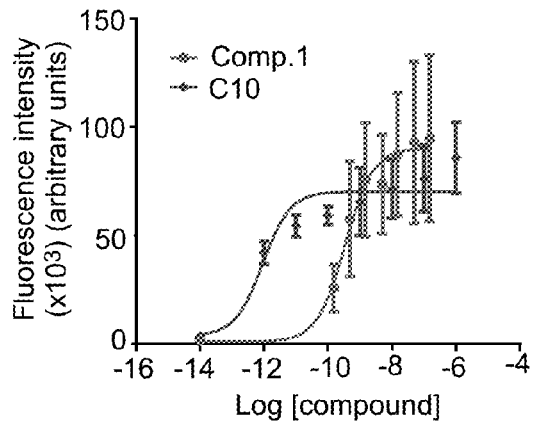
Figure 5D:
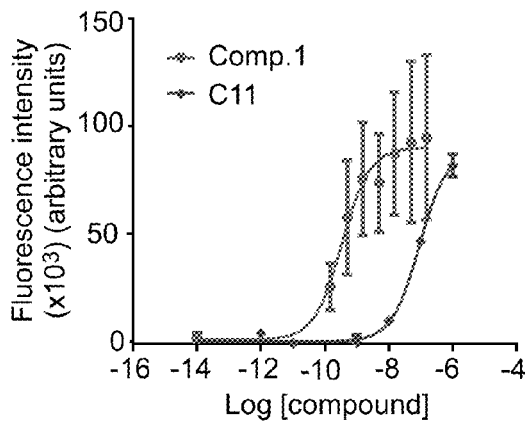
Figure 5E:
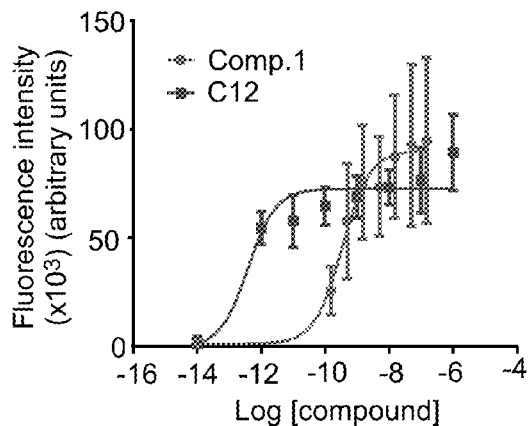
Figure 5F:
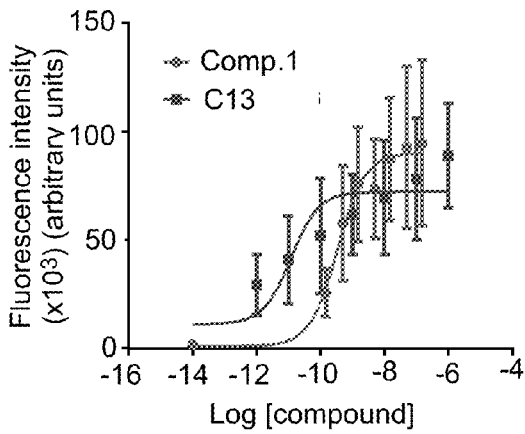
Figure 5G:
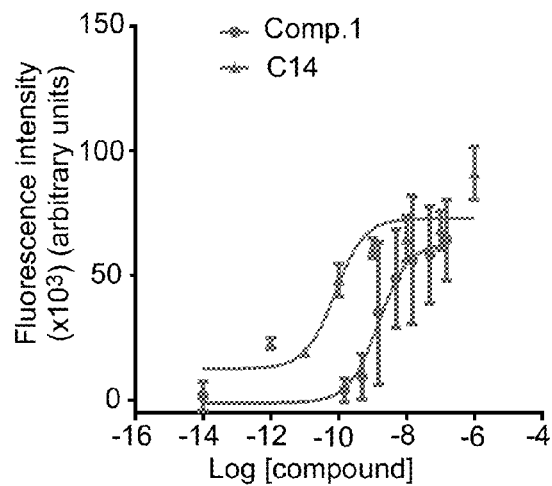
Figure 5H:
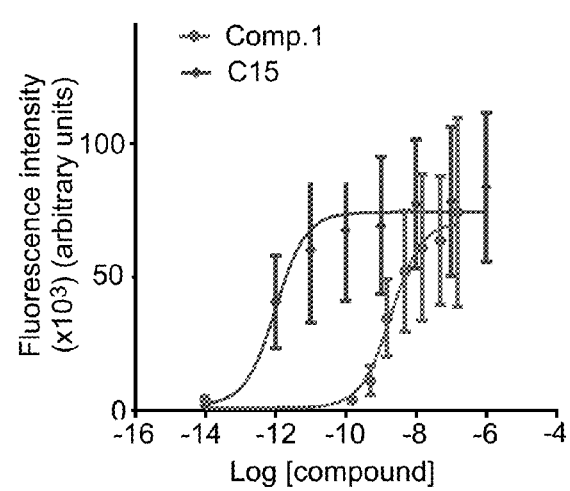
Figure 5I:
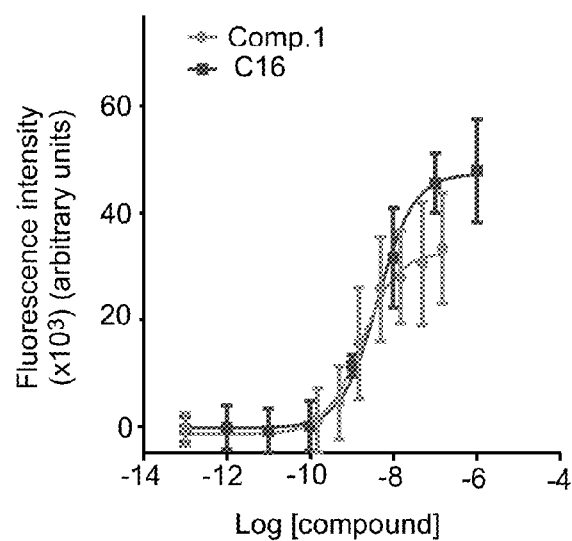
Figure 6A:
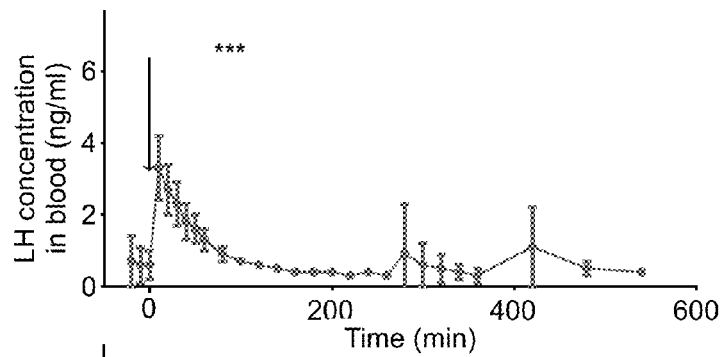
FIGS. 6a to 6d show the concentration of LH measured in blood samples taken from ewes in the anestrus period, at various times before and after the intravenous administration of physiological solutions containing, respectively, 5 nmol/ewe of the compounds.
Figure 6B:
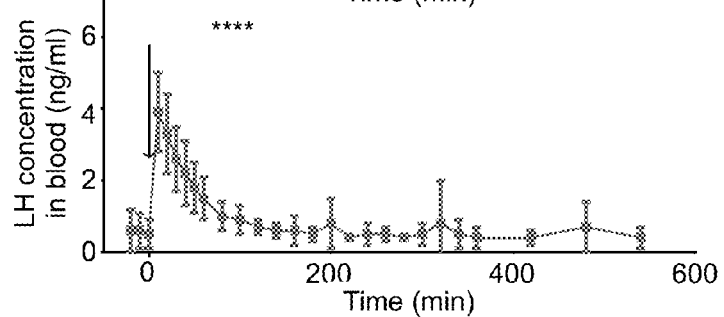
Figure 6C:
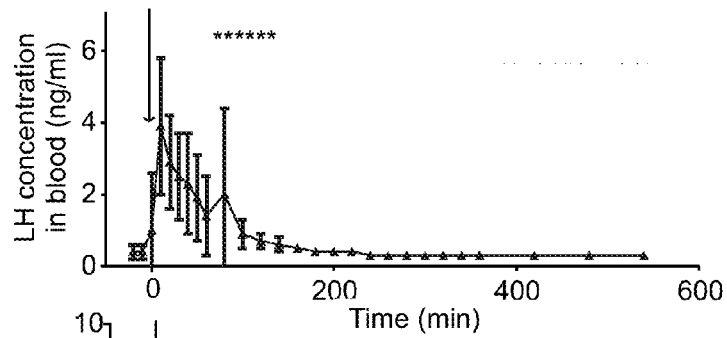
Figure 6D:
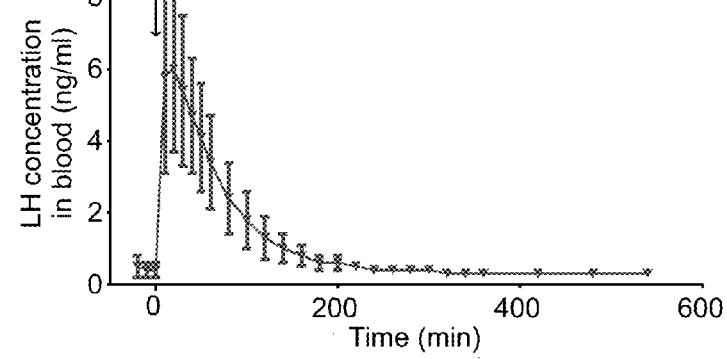

The results obtained, in terms of LH concentration in each blood sample, related to the maximum LH concentration measured after injection of 5 nmol/ewe of Comp.1 (% of Comp.1 maximum stimulation), as a function of time, are shown in FIG. 3 for the compounds Comp.1 and Comp.3 (ewes in the anestrus period) and in FIG. 4 for the compounds Comp.1, C1, C4 and C6 (ewes in the estrus period).

It emerges clearly from these figures that the compounds in accordance with the invention C1, C4 and C6 are all more active than the comparative compounds Comp.1 and Comp.3 with regard to the increase in the plasma concentration of LH.

More particularly, it is observed in FIG. 3 that the compound which has an N-terminal substitution (Comp.3), which is more powerful than Comp.1 (mKP10) in vitro, only minimally increases, in this in vivo test, the efficiency and the duration of the elevation of the plasma LH concentration. On the other hand, as can be observed in FIG. 4, the introduction of a triazole unit as a replacement for the peptide bond between the glycine and leucine residues, in accordance with the present invention, very substantially increases not only the plasma LH concentration, but also the duration of this increase.

4.2/ $2^{nd}$ Experiment

In this example, the compounds in accordance with the invention C1 and C2 and the comparative compounds Comp.1 and Comp.3 were tested.

The tests were carried out on ewes of the Ile de France breed in the anestrus period, in the same way as above with reference to the $1^{st}$ experiment (without any treatment with progesterone). In particular, for all the animals, the day before the test, a catheter was inserted into the jugular vein of the animal. On the day of the test, the peptide compound to be tested was injected into the catheter, at the desired dose (5 nmol/ewe), diluted in 1 ml of physiological solution.

The results obtained, in terms of LH concentration in each blood sample as a function of time, are shown in FIGS. 6a to 6d, respectively for the compounds Comp.1, Comp.3, C1 and C2. In these figures, the arrow, showing the time "0", indicates the moment of the injection. The duration of action of the compound concerned is symbolized by asterisks, the number of which is proportional to the duration of action of the compound.

It emerges clearly from these figures that the compounds in accordance with the invention C1 and C2 have a duration of action which is sustained for longer over time than the comparative compounds Comp.1 and Comp.3, from which they differ respectively only by the replacement of the peptide bond between the glycine and leucine residues with the 1,4-disubstituted 1,2,3-triazole bond.

Figure 7:
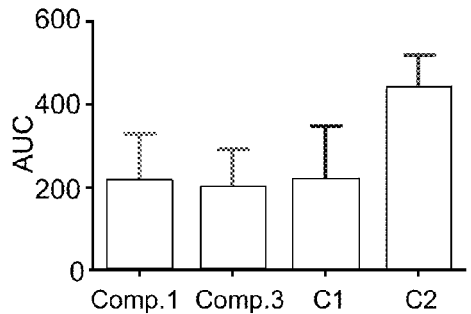
FIG. 7 is a histogram showing the area under the curve (AUC) calculated for each curve of FIGS. 6a to 6d.

For each of the curves obtained, the area under the curve (AUC) was calculated. All of the values obtained are shown in FIG. 7. It is observed therein that the compound according to the invention C2 is significantly more active than the comparative compounds with regard to the total increase in the plasma LH concentration over the whole of the duration of the experiment (9 hours).

4.3/ $3^{rd}$ Experiment

Tested in this example were the compounds in accordance with the invention C2 and C8, which differ by the presence in C8, of a unit capable of binding to serum albumin at position 2 of the peptide compound.

The tests were carried out on ewes of the Ile de France breed in the anestrus period, as indicated above with reference to the 1st experiment (without any treatment with progesterone). In particular, for all the animals, the day before the test, a catheter was inserted into the jugular vein of the animal. On the day of the test, the peptide compound to be tested was injected into the catheter, at the desired dose, diluted in 1 ml of physiological solution. For each compound, the following three doses were tested: 1 nmol/ewe, 5 nmol/ewe and 15 nmol/ewe.

Figure 8A:
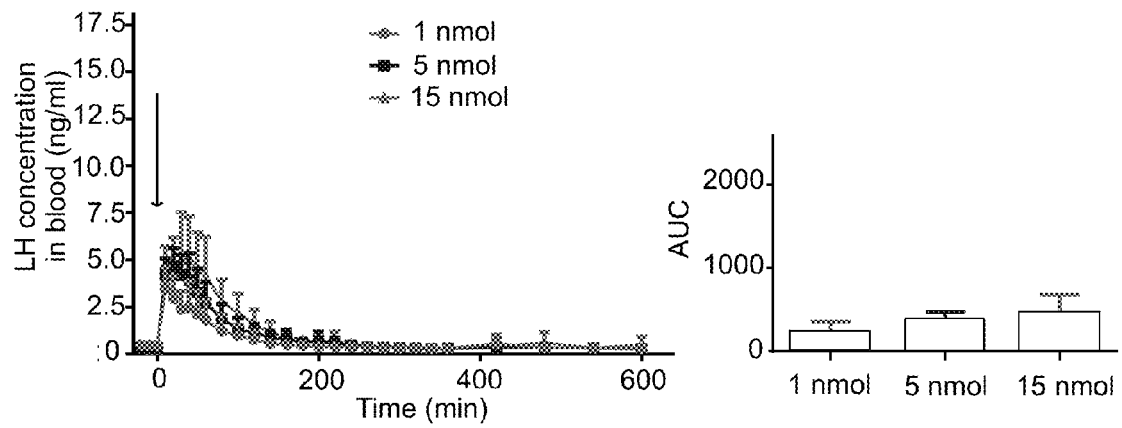
FIGS. 8a and 8b show the concentration of LH measured in blood samples taken from ewes in the anestrus period, at various times before and after the intravenous administration of physiological solutions containing, respectively, the compounds according to the invention.
Figure 8B:
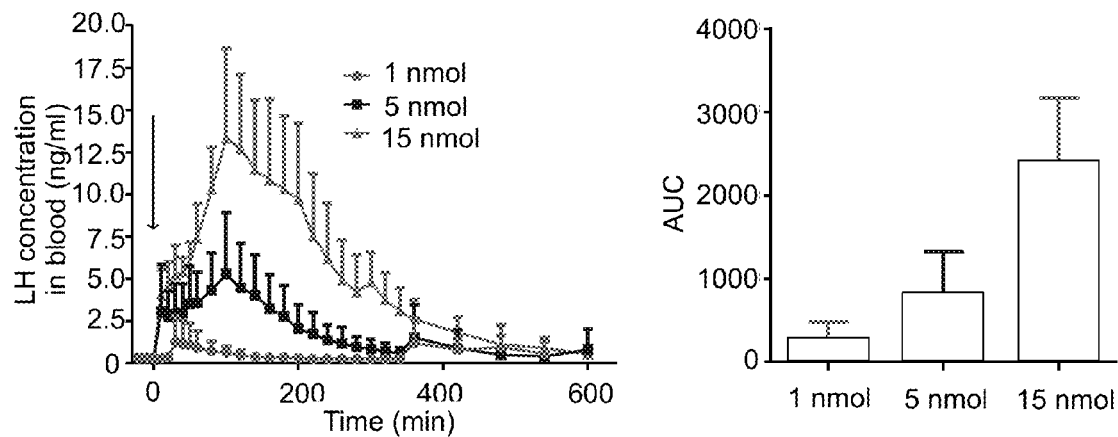

The results obtained, in terms of LH concentration in each blood sample as a function of time, for each dose injected, are shown in FIGS. 8a and 8b, respectively for the compounds C2 and C8. In these figures, the arrow, showing the time "0", indicates the moment of the injection.

It emerges clearly from these figures that the compound in accordance with the invention C8, which differs from the compound C2 by virtue of the introduction of a unit capable of binding to serum albumin, has an action which is even further sustained over time, and very significantly, than the compound C2, which was itself demonstrated above to be much more effective than the comparative compounds Comp.1 and Comp.3.

Figure 9A:
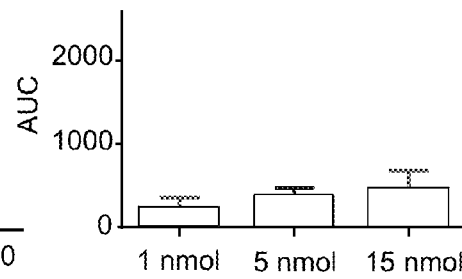
FIGS. 9a and 9b are histograms showing the area under the curve (AUC) calculated for each of the curves, respectively, of FIGS. 8a and 8b.
Figure 9B:
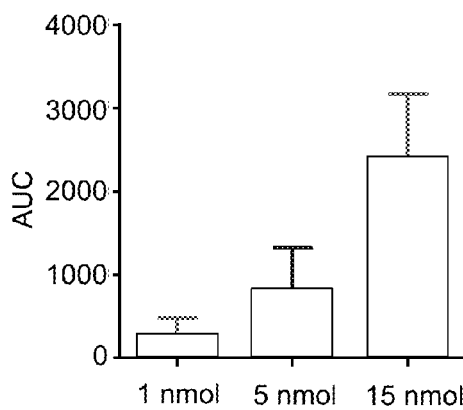

For each of the curves obtained, the area under the curve (AUC) was calculated. All of the values obtained are shown in FIGS. 9a and 9b, respectively for the compounds C2 and C8. It is observed therein that the compound according to the invention C8 is even more active than the compound C2 with regard to LH secretion.

4.4/ 4th Experiment

In this example, the compound in accordance with the invention C8 was injected, on the one hand, intravenously and, on the other hand, intramuscularly, into ewes of the Ile de France breed in the estrus period.

The ewes were pretreated with a vaginal sponge containing 20 mg of fluorogestone acetate (Chronogest CR sponge, Intervet) in order to block LH secretion and to stimulate a luteal phase.

In this experiment, a vaginal sponge leave-in time that was longer compared with the 1st experiment was chosen, so as to obtain better blocking of the endogenous pulsatility of LH. Twelve days after insertion of the sponge, a catheter was inserted into the jugular vein of some of the animals. On the day of the test, the compound C8 was injected into the catheter, at the desired dose (15 nmol/ewe), diluted in 1 ml of physiological solution. Physiological saline containing heparin (3 ml) was injected immediately after the peptide compound in order to rinse the catheter and to carry all of the compound into the animal's bloodstream.

In parallel, on other animals, on the same day, an intramuscular injection was carried out, at the same dose (15 nmol/ewe), into the muscles of the animals located between the neck and the shoulder, as performed on farms.

Before and following the injection of the test compound, blood samples were taken at variable intervals between 10 min and 1 h, for a period of 10 h.

The blood samples were centrifuged, and the plasma was stored at −20° C. until it was used to measure the LH concentration, according to the RIA method described in the literature (Caraty et al., 2007).

Figure 10:
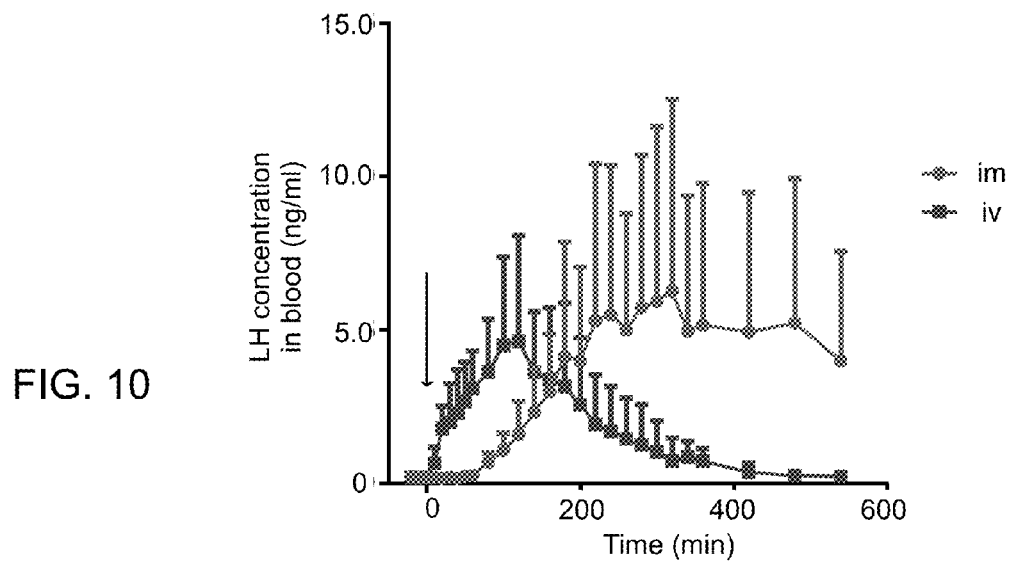
FIG. 10 shows the concentration of LH measured in blood samples taken from ewes in the estrus period, at various times before and after the injection of a physiological solution containing the compound according to the invention C8 at a concentration of 15 nmol/ewe, on the one hand, intravenously (iv) and, on the other hand, intramuscularly (im).

The results obtained, in terms of LH concentration in each blood sample, are shown in FIG. 10. In this figure, the arrow, showing the time "0", indicates the moment of the injections. These results show that the peptide compound according to the invention C8 is also effective, in vivo, by intramuscular injection, on LH secretion into the plasma.

LITERATURE REFERENCES

Angelini et al., 2012, *J. Med. Chem.*, 55: 10187-10197
Caraty et al., 2007, *Endocrin.* 148(11): 5258-5267
Caraty and Franceschini, 2008, *Reprod. Dom. Anim. (Suppl. 2)*: 172-178
Dennis et al., 2002, *J. Biol. Chem.*, 277: 35035-35043.
Dumelin et al., 2008, *Angew. Chem., Int. Ed.*, 47: 3196-3201
Goddard-Borger and Stick, 2007, *Org. Lett.* 9: 3797-3800
Knudsen et al., 2000, *J. Med. Chem.* 43: 1664-1669
Kotani et al., 2011, *J. Biol. Chem.* 276(37): 34631-34636
Mancini et al., 2009, *British Journal of Pharmacology*, 158(1): 382-391
Pokorski et al., 2007, *Org. Lett.* 9: 2381-2383
Reginato et al., 1996, *Tetrahedron* 52: 10985-10996
Sébert et al., 2010, *Domest. Anim. Endocrinol.* 38(4): 289-298
Seminara et al., 2006, *Endocrinology* 147(5): 2122-2126
Trüssel et al., 2009, *Bioconjugate Chem.*, 20: 2286-2292
Zarandi et al., 2006, *Proc. Natl. Acad. Sci. USA*, 103(12): 4610-4615
Zhang et al., 2013, *Nature* 497(7448): 211-216

The invention claimed is:

1. A KISS1R receptor agonist peptide compound, selected from:

a pseudopeptide comprising the C-terminal sequence:

-Xaa1Ψ[Tz] Xaa2-Xaa3-Xaa4-NH$_2$  (SEQ ID NO: 3)

wherein

Ψ[Tz] represents a 1,4-disubstituted 1,2,3-triazole group of formula (I)

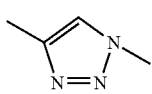

(I)

replacing the peptide bond between the Xaa1 residue and the Xaa2 residue,

Xaa1 represents Gly or Ala,

Xaa2 represents Leu or an aliphatic α-aminoacyl analog residue,

Xaa3 represents Arg, the —NH$_2$ function of which is optionally substituted with a methyl group, or Xaa3 represents a positively charged α-aminoacyl analog residue, and Xaa4 represents Tyr, Phe, Trp or an α-aminoacyl analog residue of aryl alanine type;

an analog of said pseudopeptide comprising the C-terminal sequence SEQ ID NO: 3, in which the amide peptide bond between Xaa2 and Xaa3 and/or between Xaa3 and Xaa4 is replaced with an isosteric bond;

or a salt of said pseudopeptide or said analog.

2. The peptide compound according to claim 1, selected from:

the pseudopeptide of sequence:

Tyr-Asn-Trp-Asn-Ser-Phe-Xaa1Ψ[Tz]Xaa2-Xaa3-Xaa4-NH$_2$  (SEQ ID NO: 4);

an analog of said pseudopeptide capable of binding the KISS1R receptor;
or a salt of said pseudopeptide or said analog.

3. The peptide compound according to claim 2, wherein the compound is the analog of said pseudopeptide of sequence SEQ ID NO: 4, in which at least one amino acid selected from Tyr1, Asn2 and Trp3 is replaced with a lysine (Lys).

4. The peptide compound according to claim 3, wherein the amine function of said lysine is substituted with one or more groups selected from an alkanoyl group, a polyalkylene glycol chain, and a lipid chain.

5. The peptide compound according to claim 2, wherein the compound is the analog of said pseudopeptide of sequence SEQ ID NO: 4, in which the amino acid Tyr1 is replaced with its D enantiomer.

6. The peptide compound according to claim 1, wherein the N-terminal amine function is modified by substitution with a group selected from linear alkanoyls, a benzoyl group and a tetramethylguanidinium group.

7. The peptide compound according to claim 1, wherein the N-terminal amine function is replaced with an azide function or with the 1,4-disubstituted 1,2,3-triazole group of formula (I).

8. The peptide compound according to claim 1, wherein the N-terminal amine function is substituted with an alkyl group or with a benzyl group.

9. The peptide compound according to claim 8, wherein said alkyl group is a linear alkyl.

10. The peptide compound according to claim 1, wherein at least one amino acid is bonded to one or more polyalkylene glycol chains, one or more lipid chains, and/or one or more groups that bind to serum albumin.

11. The peptide compound according to claim 1, wherein at least one amino acid is bonded to a group capable of binding to serum albumin.

12. The peptide compound according to claim 1, wherein at least one amino acid is bonded to a γ-(N-hexadecanoyl-Glu-OH) group.

13. A pharmaceutical or veterinary composition, comprising the peptide compound according to claim 1 in a pharmaceutically acceptable carrier.

14. The composition according to claim 13, in a form to be administered by intramuscular, subcutaneous, intravenous or intradermal injection, or in an orally administrable form.

15. A medicament, comprising the peptide compound according to claim 1.

16. The medicament according to claim 15, in a form to be administered as an injection.

* * * * *